(12) United States Patent
Brown et al.

(10) Patent No.: US 11,324,738 B2
(45) Date of Patent: *May 10, 2022

(54) MUSCARINIC AGONISTS

(71) Applicant: Heptares Therapeutics Limited, Cambridge (GB)

(72) Inventors: Giles Albert Brown, Cambridge (GB); Miles Stuart Congreve, Cambridge (GB); Mark Pickworth, Cambridge (GB); Mark David Rackham, Cambridge (GB); Benjamin Gerald Tehan, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/728,762

(22) Filed: Dec. 27, 2019

(65) Prior Publication Data

US 2020/0129496 A1    Apr. 30, 2020

Related U.S. Application Data

(62) Division of application No. 15/749,743, filed as application No. PCT/GB2016/052384 on Aug. 3, 2016, now Pat. No. 10,548,884.

(30) Foreign Application Priority Data

Aug. 3, 2015 (GB) .................................. 1513740

(51) Int. Cl.
*A61P 25/14* (2006.01)
*A61P 25/28* (2006.01)
*C07D 401/14* (2006.01)
*C07D 413/14* (2006.01)
*A61K 31/4523* (2006.01)

(52) U.S. Cl.
CPC .......... *A61K 31/4523* (2013.01); *A61P 25/14* (2018.01); *A61P 25/28* (2018.01); *C07D 401/14* (2013.01); *C07D 413/14* (2013.01)

(58) Field of Classification Search
CPC ................ C07D 413/14; C07D 401/14; A61K 31/4523; A61P 25/14; A61P 25/28
See application file for complete search history.

(56) References Cited

U.S. PATENT DOCUMENTS

| | | | |
|---|---|---|---|
| 9,670,183 B2* | 6/2017 | Brown | A61P 25/04 |
| 9,926,297 B2* | 3/2018 | Brown | A61P 25/18 |
| 10,196,380 B2* | 2/2019 | Brown | A61P 25/02 |
| 10,385,039 B2* | 8/2019 | Brown | C07D 417/14 |
| 10,548,884 B2* | 2/2020 | Brown | A61K 31/4523 |
| 10,689,368 B2* | 6/2020 | Brown | A61P 25/04 |
| 10,738,029 B2* | 8/2020 | Brown | C07D 401/14 |
| 10,961,225 B2* | 3/2021 | Brown | C07D 401/14 |
| 2018/0222885 A1 | 8/2018 | Brown et al. | |

FOREIGN PATENT DOCUMENTS

| | | |
|---|---|---|
| WO | 2007/100664 A2 | 9/2007 |
| WO | 2007/100670 A1 | 9/2007 |
| WO | 2010/049146 A1 | 5/2010 |
| WO | 2010/130945 A1 | 11/2010 |
| WO | 2013/072705 A1 | 5/2013 |
| WO | 2014/045031 A1 | 3/2014 |
| WO | 2015/118342 A1 | 8/2015 |

OTHER PUBLICATIONS

International Search Report and Written Opinion for Application No. PCT/GB2016/052384, dated Nov. 3, 2016.
United Kingdom Search Report for Application No. GB1513740.9, dated May 11, 2016.
United Kingdom Search Report for Application No. GB1416625.0, dated Jun. 3, 2015.

* cited by examiner

*Primary Examiner* — Amanda L. Aguirre
(74) *Attorney, Agent, or Firm* — Fish & Richardson P.C.

(57) ABSTRACT

This invention relates to compounds that are agonists of the muscarinic $M_1$ receptor and/or $M_4$ receptor and which are useful in the treatment of muscarinic $M_1/M_4$ receptor mediated diseases. Also provided are pharmaceutical compositions containing the compounds and the therapeutic uses of the compounds. Compounds include those according to formula 1a

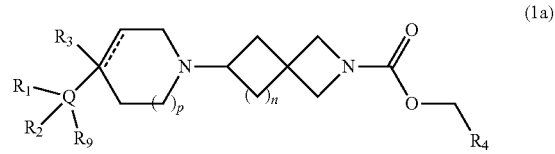

(1a)

or a salt thereof, wherein n, p, Q, $R^1$, $R^2$, $R^3$, $R^9$ and $R^4$ are as defined herein.

18 Claims, No Drawings

MUSCARINIC AGONISTS

RELATED APPLICATIONS

This application is a divisional application of U.S. application Ser. No. 15/749,743, filed Feb. 1, 2018, which is a 371 U.S. national stage filing, under 35 U.S.C. § 371(c), of International Application No. PCT/GB2016/052384, filed Aug. 3, 2016, which claims priority to United Kingdom Application No. 1513740.9, filed Aug. 3, 2015. The entire contents of each of the aforementioned applications are incorporated herein by reference in their entirety.

This invention relates to compounds that are agonists of the muscarinic $M_1$ receptor and/or $M_4$ receptor and which are useful in the treatment of muscarinic $M_1/M_4$ receptor mediated diseases. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 Br J Pharmacol). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 Br J Pharmacol).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 Science). In schizophrenia, which also has cognitive impairment as an important component of the clinical picture, mAChR density is reduced in the pre-frontal cortex, hippocampus and caudate putamen of schizophrenic subjects (Dean et al., 2002 Mol Psychiatry).

Furthermore, in animal models, blockade or damage to central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting adverse events resulting from stimulation of peripheral $M_2$ and $M_3$ mAChRs including disturbed gastrointestinal motility, bradycardia, nausea and vomiting (www.drugs.com/pro/donepezil.html; www.drugs.com/pro/rivastigmine.html).

Further discovery efforts have targeted the identification of direct $M_1$ mAChR agonists with the aim of inducing selective improvements in cognitive function with a favourable adverse effect profile. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain pathologies: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidgenic and amyloidgenic. Cleavage of APP by γ-secretase is common to both pathways, but in the former APP is cleaved by an α-secretase to yield soluble APPα. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 Neuron). The mAChR agonist cevimeline has been shown to give a small, but significant, reduction in cerebrospinal fluid levels of Aβ in Alzheimer's patients, thus demonstrating potential disease modifying efficacy (Nitsch et al., 2000 Neurol).

Preclinical studies have suggested that mAChR agonists display an atypical antipsychotic-like profile in a range of pre-clinical paradigms. The mAChR agonist, xanomeline, reverses a number of dopamine mediated behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 CNS Drug Rev).

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic adverse events, including nausea, gastrointestinal pain, diahorrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage; however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

THE INVENTION

The present invention provides compounds having activity as muscarinic $M_1$ and/or $M_4$ receptor agonists. More particularly, the invention provides compounds that exhibit selectivity for the $M_1$ receptor and/or the $M_4$ receptor relative to the $M_2$ and $M_3$ receptor subtypes.

Accordingly, in a first embodiment (Embodiment 1.1), the invention provides a compound of the formula (1) or formula (1a):

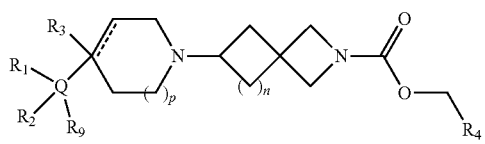

or a salt thereof, wherein
n is 1 or 2
p is 0, 1 or 2

Q is a five, six or seven membered monocyclic heterocyclic ring containing 1, 2, 3 or 4 heteroatom ring members selected from N, O and S;

$R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

$R^2$ is selected from hydrogen; fluorine; chlorine; bromine; cyano; hydroxy; methoxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group; or $R^1$ and $R^2$ can be joined together to form a 6 membered fused aromatic ring;

$R^9$ is selected from hydrogen, $CH_3$, $CH_2OH$, $CH(CH_3)OH$, $C(CH_3)_2OH$ and $COOCH_3$;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$, $R^6$ and $R^7$ are the same or different and each is independently selected from hydrogen, a non-aromatic $C_{1-4}$ hydrocarbon group optionally substituted with one or more fluorine atoms; or a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine; chlorine; bromine; cyano; hydroxy; methoxy; amino; or a cycloalkyl, heterocycloalkyl, aryl or heteroaryl group;

and the dotted line indicates an optional second carbon-carbon bond, provided that when a second carbon-carbon bond is present, then $R^3$ is absent.

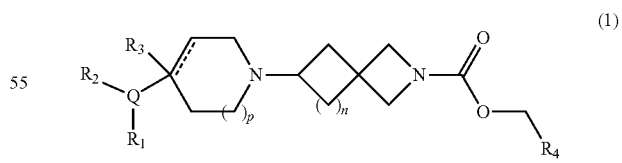

or a salt thereof, wherein
n is 1 or 2
p is 0, 1 or 2

Q is a five, six or seven membered monocyclic heterocyclic ring containing 1, 2, 3 or 4 heteroatom ring members selected from N, O and S;

$R^1$ is selected from hydrogen; fluorine; chlorine; bromine; cyano; oxo; hydroxy; $OR^5$; $NR^5R^6$; $COR^5$; $COOR^5$;

OCOR$^5$; NR$^7$COR$^5$; CONR$^5$R$^6$; NR$^7$CONR$^5$R$^6$; NR$^7$COOR$^5$; OCONR$^5$R$^6$; SR$^5$; SOR$^5$ and SO$_2$R$^5$; a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

R$^2$ is selected from hydrogen; fluorine; chlorine; bromine; cyano; hydroxy; methoxy; OR$^5$; NR$^5$R$^6$; COR$^5$; COOR$^5$; OCOR$^5$; NR$^7$COR$^5$; CONR$^5$R$^6$; NR$^7$CONR$^5$R$^6$; NR$^7$COOR$^5$; OCONR$^5$R$^6$; SR$^5$; SOR$^5$ and SO$_2$R$^5$; a C$_{1-6}$ non-aromatic hydrocarbon group; or R$^1$ and R$^2$ can be joined together to form a 6 membered fused aromatic ring;

R$^3$ is selected from hydrogen; fluorine; cyano; hydroxy; amino; and a C$_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

R$^4$ is a hydrogen or a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

R$^5$, R$^6$ and R$^7$ are the same or different and each is independently selected from hydrogen, a non-aromatic C$_{1-4}$ hydrocarbon group optionally substituted with one or more fluorine atoms; or a group of formula CH$_2$N(R$^a$)COOR$^b$;

R$^a$ is selected from hydrogen and a non-aromatic C$_{1-4}$ hydrocarbon group;

R$^b$ is a non-aromatic C$_{1-4}$ hydrocarbon group which is optionally substituted with one or more groups selected from fluorine; chlorine; bromine; cyano; hydroxy; methoxy; amino; or a cycloalkyl, heterocycloalkyl, aryl or heteroaryl group;

and the dotted line indicates an optional second carbon-carbon bond, provided that when a second carbon-carbon bond is present, then R$^3$ is absent.

Particular compounds of the formula (1) or formula (1a), are as defined in the Embodiments 1.2 to 1.180 set out below.

1.2 A compound according to Embodiment 1.1 wherein Q is an aromatic or unsaturated heterocyclic ring.

1.3 A compound according to Embodiment 1.2 wherein Q is an aromatic heterocyclic ring.

1.4 A compound according to Embodiment 1.3 wherein Q is an aromatic heterocyclic ring containing a nitrogen ring member and optionally one or two further ring members selected from O, N and S.

1.5 A compound according to Embodiment 1.4 wherein Q is an aromatic heterocyclic ring containing a nitrogen ring member and optionally one further ring member selected from O, N and S.

1.6 A compound according to Embodiment 1.5 wherein Q is an aromatic heterocyclic ring containing one or two nitrogen ring members.

1.7 A compound according to any one of Embodiments 1.1 to 1.6 wherein Q is a five membered heterocyclic ring linked to the adjacent six-membered ring by a carbon atom of the said five membered heterocylic ring.

1.8 A compound according to any one of Embodiments 1.1 to 1.6 wherein Q is a five membered heterocyclic ring linked to the adjacent six-membered ring by a nitrogen atom of the said five membered heterocylic ring.

1.9 A compound according to Embodiment 1.1 wherein Q is selected from 1-pyrrolyl, 2-imidazolyl, 1-pyrazolyl, 3-pyrazolyl, 5-pyrazolyl, 2-thiazolyl, 2-oxazolyl, triazolyl, tetrazolyl, thiadiazolyl, oxadiazolyl, and tautomeric forms thereof.

1.10 A compound according to Embodiment 1.6 wherein Q is a pyrrole ring.

1.11 A compound according to Embodiment 1.6 wherein Q is an imidazole ring 1.12 A compound according to Embodiment 1.6 wherein Q is a pyrazole ring.

1.13 A compound according to Embodiment 1.6 wherein Q is selected from 1-pyrazolyl, 3-pyrazolyl, 5-pyrazolyl and tautomeric forms thereof.

1.14 A compound according to Embodiment 1.1 wherein Q is a 6 membered ring containing one or more nitrogen atoms.

1.15 A compound according to Embodiment 1.14 wherein Q is pyridyl, pyrazyl or a 2-oxo-3N (3-piperidin-2-one) ring containing 0-2 C—C unsaturated bonds.

1.16 A compound according to Embodiment 1.1 wherein Q is a 5, 6 or 7 membered unsaturated heterocyclic ring.

1.17 A compound according to Embodiment 1.16 wherein Q is 5-pyrollidinyl.

1.18 A compound according to any one of Embodiments 1.1 to 1.17 wherein R$^1$ is selected from hydrogen; fluorine; chlorine; bromine; cyano; oxo; hydroxy; OR$^5$; NR$^5$R$^6$; COR$^5$, COOR$^5$; OCOR$^5$; NR$^7$COR$^5$; CONR$^5$R$^6$; NR$^7$CONR$^5$R$^6$; NR$^7$COOR$^5$; OCONR$^5$R$^6$; SR$^5$; SOR$^5$ and SO$_2$R$^5$; a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group R$^8$ consisting of hydrogen; fluorine; chlorine; bromine; cyano; oxo; hydroxy; OR$^5$; NR$^5$R$^6$; COR$^5$; COOR$^5$; OCOR$^5$; NR$^7$COR$^5$; CONR$^5$R$^6$; NR$^7$CONR$^5$R$^6$; NR$^7$COOR$^5$; OCONR$^5$R$^6$; SR$^5$; SOR$^5$ and SO$_2$R$^5$; and a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.19 A compound according to Embodiment 1.18 wherein R$^1$ is selected from hydrogen; fluorine; chlorine; bromine; cyano; oxo; hydroxy; OR$^5$; NR$^5$R$^6$; COR$^5$; COOR$^5$; OCOR$^5$; NR$^7$COR$^5$; CONR$^5$R$^6$; NR$^7$CONR$^5$R$^6$; NR$^7$COOR$^5$; OCONR$^5$R$^6$; SR$^5$; SOR$^5$ and SO$_2$R$^5$; a C$_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1 or 2 heteroatoms selected from O, N and S and oxidized forms thereof;

wherein the optional substituents for the optionally substituted 5- or 6-membered ring are selected from a group R$^8$ consisting of fluorine; chlorine; bromine; cyano; oxo; hydroxy; OR$^5$; NR$^5$R$^6$; COR$^5$; COOR$^5$;

OCOR⁵; NR⁷COR⁵; CONR⁵R⁶; NR⁷CONR⁵R⁶; NR⁷COOR⁵; OCONR⁵R⁶; SR⁵; SOR⁵ and SO₂R⁵; and a C₁₋₄ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.20 A compound according to Embodiment 1.19 wherein R¹ is selected from hydrogen; fluorine; chlorine; bromine; cyano; oxo; hydroxy; OR⁵; NR⁵R⁶; COR⁵; COOR⁵; OCOR⁵; NR⁷COR⁵; CONR⁵R⁶; NR⁷CONR⁵R⁶; NR⁷COOR⁵; OCONR⁵R⁶; SR⁵; SOR⁵ and SO₂R⁵; a C₁₋₄ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered aryl or heteroaryl ring containing 0, 1 or 2 heteroatoms selected from O, N and S and oxidized forms thereof;
wherein the optional substituents for the optionally substituted 5- or 6-membered aryl or heteroaryl ring are selected from a group R⁸ consisting of fluorine; chlorine; bromine; cyano; oxo; hydroxy; OR⁵; NR⁵R⁶; COR⁵; COOR⁵; OCOR⁵; NR⁷COR⁵; CONR⁵R⁶; NR⁷CONR⁵R⁶; NR⁷COOR⁵; OCONR⁵R⁶; SR⁵; SOR⁵ and SO₂R⁵; and a C₁₋₄ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.21 A compound according to any one of Embodiments 1.1 to 1.17 wherein R¹ is selected from hydrogen; fluorine; chlorine; cyano; oxo; hydroxy; OR⁵; NR⁵R⁶; COR⁵; COOR⁵; OCOR⁵; NR⁷COR⁵; CONR⁵R⁶; NR⁷CONR⁵R⁶; NR⁷COOR⁵; OCONR⁵R⁶; SO₂R⁵; a C₁₋₄ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof, wherein the optional substituents for the optionally substituted 5- or 6-membered ring are selected from a group R⁸ consisting of fluorine; chlorine; bromine; cyano; oxo; hydroxy; OR⁵; NR⁵R⁶; COR⁵; COOR⁵; OCOR⁵; NR⁷COR⁵; CONR⁵R⁶; NR⁷CONR⁵R⁶; NR⁷COOR⁵; OCONR⁵R⁶; SR⁵; SOR⁵ and SO₂R⁵; and a C₁₋₄ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.22 A compound according to Embodiment 1.21 wherein R¹ is selected from hydrogen; fluorine; chlorine; cyano; hydroxy; OR⁵; NR⁵R⁶; COR⁵; COOR⁵; OCOR⁵; NR⁷COR⁵; CONR⁵R⁶; NR⁷CONR⁵R⁶; NR⁷COOR⁵; OCONR⁵R⁶; SO₂R⁵; and a C₁₋₄ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.23 A compound according to Embodiment 1.22 wherein R¹ is selected from hydrogen; fluorine; chlorine; cyano; hydroxy; OR⁵; NR⁵R⁶; COR⁵; COOR⁵; OCOR⁵; NR⁷COR⁵; CONR⁵R⁶; NR⁷CONR⁵R⁶; NR⁷COOR⁵; SO₂R⁵; and a C₁₋₄ non-aromatic hydrocarbon group which is optionally substituted with one to six fluorine atoms.

1.24 A compound according to Embodiment 1.23 wherein R¹ is selected from hydrogen; fluorine; chlorine; cyano; NR⁵R⁶; COR⁵; COOR⁵ and a C₁₋₆ non-aromatic hydrocarbon group which is optionally substituted with one to six fluorine atoms.

1.25 A compound according to Embodiment 1.24 wherein R¹ is selected from hydrogen; fluorine; chlorine; cyano; NH₂, COR⁵; COOR⁵ and a C₁₋₄ saturated non-aromatic hydrocarbon group which is optionally substituted with one to six fluorine atoms.

1.26 A compound according to Embodiment 1.25 wherein R¹ is selected from hydrogen; COR⁵; COOR⁵; CONR⁵R⁶ and a C₁₋₄ alkyl group.

1.27 A compound according to Embodiment 1.26 wherein R¹ is selected from hydrogen; COR⁵; COOR⁵ and a C₁₋₃ alkyl group.

1.28 A compound according to Embodiment 1.27 wherein R¹ is selected from hydrogen; methyl; ethyl and COOR⁵.

1.29 A compound according to Embodiment 1.28 wherein R¹ is hydrogen.

1.30 A compound according to Embodiment 1.28 wherein R¹ is methyl or ethyl.

1.31 A compound according to Embodiment 1.18 to 1.28 wherein R¹ is COOMe; COOEt; COMe; COEt; CONH₂; CF₃; CONHMe; CON(Me)₂; COCF₃; CO-cyclopropyl; CO-cyclobutyl; CONHEt; COH; NH₂; OMe;

1.32 A compound according to any one of the Embodiments 1.1 to 1.31 wherein R² is selected from hydrogen; fluorine; chlorine; bromine; cyano; hydroxy; methoxy; and a C₁₋₆ non-aromatic hydrocarbon group; or is joined together with R¹ to form a 6 membered fused aromatic ring.

1.33 A compound according to Embodiment 1.32 wherein R² is selected from hydrogen; fluorine; hydroxy; methoxy; and a C₁₋₆ non-aromatic hydrocarbon group.

1.34 A compound according to Embodiment 1.33 wherein R² is selected from hydrogen; fluorine; methoxy; and a C₁₋₄ saturated hydrocarbon group.

1.35 A compound according to Embodiment 1.34 wherein R² is selected from hydrogen; fluorine; methoxy; and a C₁₋₄ alkyl group.

1.36 A compound according to Embodiment 1.35 wherein R² is selected from hydrogen and a C₁₋₃ alkyl group.

1.37 A compound according to Embodiment 1.36 wherein R² is selected from hydrogen and methyl.

1.38 A compound according to Embodiment 1.32 wherein R² is joined together with R¹ to form a 6 membered fused aromatic ring which may be aryl or heteroaryl.

1.39 A compound according to Embodiments 1.1 to 1.38 wherein R⁹ is selected from hydrogen, CH₂OH, CH(CH₃)OH, C(CH₃)₂OH and COOCH₃.

1.40 A compound according to any one of Embodiments 1.1 to 1.39 wherein the dotted line represents a second carbon-carbon bond and R³ is absent.

1.41 A compound according to any one of Embodiments 1.1 to 1.39 wherein R³ is present and the optional second carbon-carbon bond is absent.

1.42 A compound according to Embodiment 1.41 wherein R³ is selected from hydrogen; fluorine; cyano; hydroxy; amino; and a C₁₋₆ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.43 A compound according to Embodiment 1.42 wherein $R^3$ is selected from hydrogen; fluorine; cyano; hydroxy; amino; and a $C_{1-6}$ non-aromatic hydrocarbon group which is optionally substituted with one to six fluorine atoms and wherein one, but not all, carbon atoms of the hydrocarbon group may optionally be replaced by a heteroatom selected from O, N and S and oxidized forms thereof.

1.44 A compound according to Embodiment 1.43 wherein $R^3$ is selected from hydrogen; fluorine; cyano; hydroxy; amino; $C_{1-4}$ alkyl and $C_{1-4}$ alkoxy, wherein the $C_{1-4}$ alkyl and $C_{1-4}$ alkoxy are each optionally substituted with one to six fluorine atoms.

1.45 A compound according to Embodiment 1.44 wherein $R^3$ is selected from hydrogen; fluorine; hydroxy and methoxy.

1.46 A compound according to Embodiment 1.45 wherein $R^3$ is hydrogen.

1.47 A compound according to any one of Embodiments 1.1 to 1.46 wherein $R^4$ is hydrogen or an acyclic $C_{1-6}$ hydrocarbon group.

1.48 A compound according to Embodiment 1.47 wherein $R^4$ is hydrogen or an acyclic $C_{1-3}$ hydrocarbon group.

1.49 A compound according to Embodiment 1.48 wherein $R^4$ is hydrogen or a $C_{1-3}$ alkyl group or a $C_{2-3}$ alkynyl group.

1.50 A compound according to Embodiment 1.49 wherein $R^4$ is selected from hydrogen, methyl, ethyl, ethynyl and 1-propynyl.

1.51 A compound according to Embodiment 1.50 wherein $R^4$ is selected from hydrogen and methyl.

1.52 A compound according to Embodiment 1.51 wherein $R^4$ is methyl.

1.53 A compound according to any one of the preceding Embodiments wherein $R^5$, when present, is a non-aromatic $C_{1-4}$ hydrocarbon group optionally substituted with one or more fluorine atoms; or a group of formula $CH_2N(R^a)COOR^b$.

1.54 A compound according to Embodiment 1.53 wherein the non-aromatic $C_{1-4}$ hydrocarbon group is a saturated $C_{1-4}$ hydrocarbon group.

1.55 A compound according to any one of Embodiments 1.1 to 1.52 wherein $R^5$, when present, is hydrogen.

1.56 A compound according to any one of Embodiments 1.1 to 1.52 wherein $R^5$, when present, is selected from hydrogen and a saturated $C_{1-4}$ hydrocarbon group.

1.57 A compound according to Embodiment 1.54 or Embodiment 1.56 wherein the saturated $C_{1-4}$ hydrocarbon group is a $C_{1-4}$ alkyl group.

1.58 A compound according to Embodiment 1.57 wherein the saturated $C_{1-4}$ hydrocarbon group is a $C_{1-3}$ alkyl group.

1.59 A compound according to Embodiment 1.58 wherein the $C_{1-3}$ alkyl group is selected from methyl, ethyl and isopropyl.

1.60 A compound according to Embodiment 1.59 wherein the $C_{1-3}$ alkyl group is ethyl.

1.61 A compound according to any one of the preceding Embodiments wherein $R^6$, when present, is a non-aromatic $C_{1-4}$ hydrocarbon group.

1.62 A compound according to Embodiment 1.61 wherein the non-aromatic $C_{1-4}$ hydrocarbon group is a saturated $C_{1-4}$ hydrocarbon group.

1.63 A compound according to any one of Embodiments 1.1 to 1.60 wherein $R^6$, when present, is hydrogen.

1.64 A compound according to any one of Embodiments 1.1 to 1.60 wherein $R^6$, when present, is selected from hydrogen and a saturated $C_{1-4}$ hydrocarbon group.

1.65 A compound according to Embodiment 1.61 or Embodiment 1.64 wherein the saturated $C_{1-4}$ hydrocarbon group is a $C_{1-4}$ alkyl group.

1.66 A compound according to Embodiment 1.65 wherein the saturated $C_{1-4}$ hydrocarbon group is a $C_{1-3}$ alkyl group.

1.67 A compound according to Embodiment 1.66 wherein the $C_{1-3}$ alkyl group is selected from methyl, ethyl and isopropyl.

1.68 A compound according to any one of the preceding Embodiments wherein $R^7$, when present, is a non-aromatic $C_{1-4}$ hydrocarbon group.

1.69 A compound according to Embodiment 1.68 wherein the non-aromatic $C_{1-4}$ hydrocarbon group is a saturated $C_{1-4}$ hydrocarbon group.

1.70 A compound according to any one of Embodiments 1.1 to 1.67 wherein $R^7$, when present, is hydrogen.

1.71 A compound according to any one of Embodiments 1.1 to 1.67 wherein $R^7$, when present, is selected from hydrogen and a saturated $C_{1-4}$ hydrocarbon group.

1.72 A compound according to Embodiment 1.69 or Embodiment 1.71 wherein the saturated $C_{1-4}$ hydrocarbon group is a $C_{1-4}$ alkyl group.

1.73 A compound according to Embodiment 1.72 wherein the saturated $C_{1-4}$ hydrocarbon group is a $C_{1-3}$ alkyl group.

1.74 A compound according to Embodiment 1.73 wherein the $C_{1-3}$ alkyl group is selected from methyl, ethyl and isopropyl.

1.75 A compound according to any one of the preceding Embodiments wherein, when $R^1$ is an optionally substituted 5- or 6-membered ring, it is selected from aromatic rings containing 0, 1 or 2 or 3 heteroatoms selected from O, N and S and oxidized forms thereof.

1.76 A compound according to Embodiment 1.75 wherein the aromatic ring is carbocyclic.

1.77 A compound according to Embodiment 1.75 wherein the aromatic ring is heterocyclic.

1.78 A compound according to any one of Embodiments 1.1 to 1.74 wherein, when $R^1$ is an optionally substituted 5- or 6-membered ring, it is selected from non-aromatic rings containing 0, 1 or 2 or 3 heteroatoms selected from O, N and S and oxidized forms thereof.

1.79 A compound according to Embodiment 1.78 wherein the non-aromatic ring is carbocyclic.

1.80 A compound according to Embodiment 1.78 wherein the non-aromatic ring is heterocyclic.

1.81 A compound according to any one of Embodiments 1.75 to 1.80 wherein the ring is a 5-membered ring.

1.82 A compound according to any one of Embodiments 1.75 to 1.80 wherein the ring is a 6-membered ring.

1.83 A compound according to any one of the preceding Embodiments wherein, when $R^1$ is an optionally substituted 5- or 6-membered ring, it is substituted with 0, 1, 2 or 3 substituents $R^8$.

1.84 A compound according to Embodiment 1.83 wherein there are 0, 1 or 2 substituents $R^8$ present.

1.85 A compound according to Embodiment 1.84 wherein there are 0 substituents $R^8$ present.

1.86 A compound according to Embodiment 1.83 wherein there is 1 substituent $R^8$ present.

1.87 A compound according to Embodiment 1.83 wherein there are 2 substituents $R^8$ present.

1.88 A compound according to any one of Embodiments 1.82, 1.83, 1.84, 1.86 and 1.87 wherein $R^8$ when present is selected from fluorine; cyano; oxo; hydroxy; $OR^5$; $NR^5R^6$;

COR$^5$; COOR$^5$; OCOR$^5$; NR$^7$COR$^5$; CONR$^5$R$^6$; SR$^5$; SOR$^5$ and SO$_2$R$^5$; and a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.89 A compound according to Embodiment 1.88 wherein R$^8$ is selected from fluorine; cyano; oxo; hydroxy; OR$^5$; NR$^5$R$^6$; COR$^5$; COOR$^5$; OCOR$^5$ and SO$_2$R$^5$; and a C$_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.90 A compound according to Embodiment 1.89 wherein R$^8$ is selected from fluorine; cyano; oxo; hydroxy; OR$^5$; NR$^5$R$^6$; and a C$_{1-4}$ non-aromatic hydrocarbon group which is optionally substituted with one to six fluorine atoms.

1.91 A compound according to Embodiment 1.90 wherein R$^8$ is selected from cyano; oxo; hydroxy; OR$^5$; NR$^5$R$^6$; and C$_{1-4}$ alkyl.

1.92 A compound according to any one of Embodiments 1.1 to 1.91 wherein p is 0.

1.93 A compound according to any one of Embodiments 1.1 to 1.91 wherein p is 1.

1.94 A compound according to any one of Embodiments 1.1 to 1.91 wherein p is 2.

1.95 A compound according to any one of Embodiments 1.1 to 1.94 wherein n is 1.

1.96 A compound according to any one of Embodiments 1.1 to 1.94 wherein n is 2.

1.97 A compound according to any one of Embodiments 1.1 to 1.39 and 1.41 to 1.52 wherein the moiety:

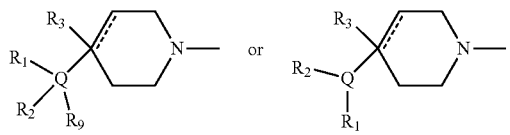

is selected from groups A to D below:

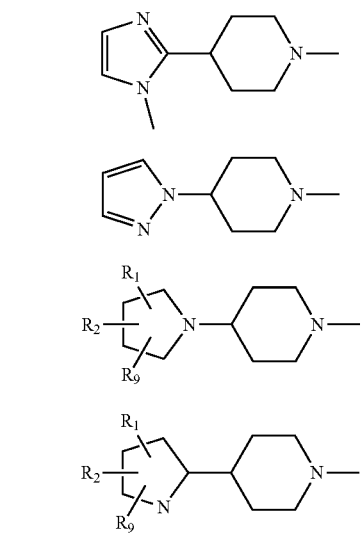

wherein R$^1$, R$^2$ and R$^9$ are as defined in any one of Embodiments 1.1 to 1.39 and 1.41 to 1.91.

1.98 A compound according to having the formula (2):

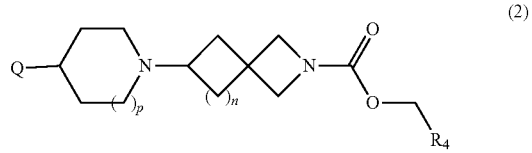

wherein n is 1 or 2, p is 0, 1 or 2, Q is an optionally substituted 5, 6 or 7 membered heterocyclic or heteroaryl ring having one or more nitrogen atoms, and R$^4$ is as defined in any one of Embodiments 1.47 to 1.52.

1.99 A compound according to Embodiments 1.1 to 1.91 having the formula (3) or (3a):

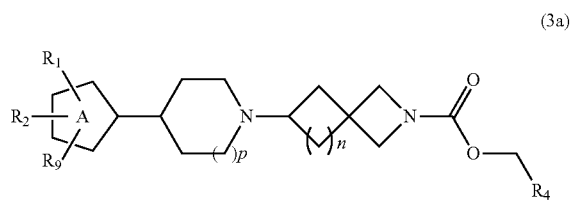

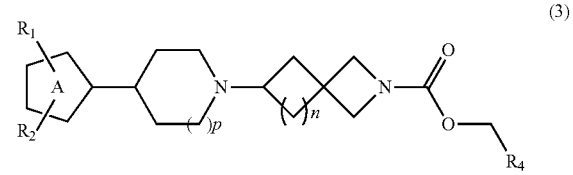

wherein n is 1 or 2, p is 0, 1 or 2, R$^1$, R$^2$, R$^9$ and R$^4$ are as defined in any one of Embodiments 1.1 to 1.39 and 1.41 to 1.91 and the ring A is a five membered heterocyclic or heteroaryl ring containing one or two nitrogen ring members.

1.100 A compound according to Embodiment 1.99 wherein the ring A is a five membered heteroaryl ring containing two nitrogen ring members.

1.101 A compound according to Embodiment 1.100 wherein the ring A is an imidazole ring.

1.102 A compound according to Embodiment 1.101 having the formula (4) or (4a):

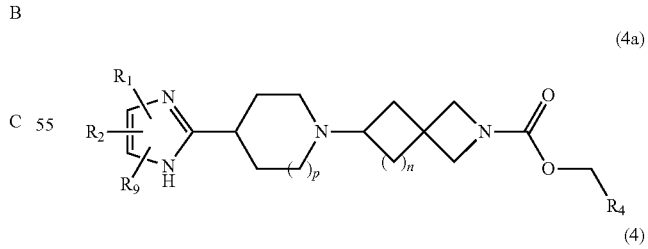

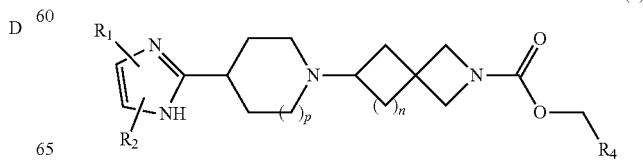

wherein n is 1 or 2, p is 0, 1 or 2, $R^1$, $R^2$, $R^9$ and $R^4$ are as defined in any one of Embodiments 1.1 to 1.39 and 1.41 to 1.91.

1.103 A compound according to Embodiment 1.100 wherein the ring A is a pyrazole ring.

1.104 A compound according to Embodiment 1.103 having the formula (5) or (5a):

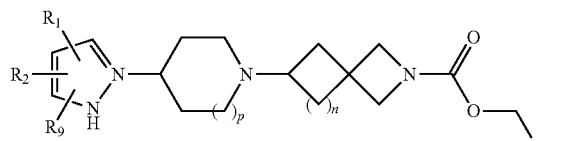

(5a)

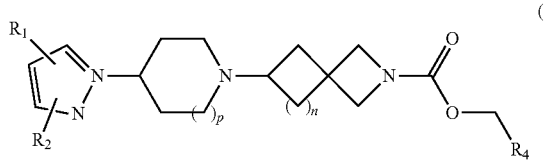

(5)

wherein n is 1 or 2, p is 0, 1 or 2, $R^1$, $R^2$, $R^9$ and $R^4$ are as defined in any one of Embodiments 1.1 to 1.39 and 1.41 to 1.91.

1.105 A compound according to Embodiment 1.94 wherein ring A is a 5 membered heterocyclic ring containing one nitrogen atom.

1.106 A compound according to Embodiment 1.100 having the formula (6) or (6a):

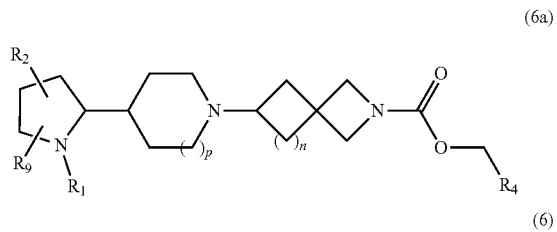

(6a)

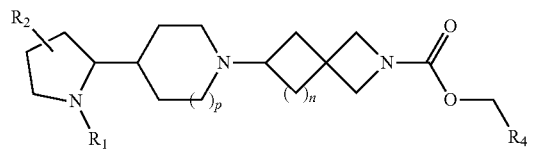

(6)

wherein n is 1 or 2, p is 0, 1 or 2, $R^1$, $R^2$, $R^9$ and $R^4$ are as defined in any one of Embodiments 1.1 to 1.39 and 1.41 to 1.91.

1.107 A compound according to embodiment 1.106 wherein the moiety:

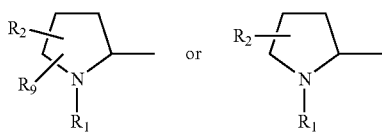

is:

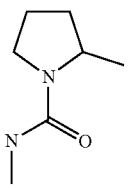

1.108 A compound according to embodiment 1.1 wherein Q is a five membered monocyclic heterocyclic ring containing 1, 2, 3 or 4 heteroatom ring members selected from N, O and S.

1.109 A compound according to Embodiment 1.1 which is as defined in any one of Examples 1-1 to 2.12.

1.110 A compound according to any one of Embodiments 1.1 to 1.104 having a molecular weight of less than 550.

1.111 A compound according to Embodiment 1.110 having a molecular weight of less than 500.

1.112 A compound according to Embodiment 1.111 having a molecular weight of, or less than 450.

1.113 A compound according to any one of Embodiments 1.1 to 1.112 which is in the form of a salt.

1.114 A compound according to Embodiment 1.113 wherein the salt is an acid addition salt.

1.115 A compound according to Embodiment 1.113 or Embodiment 1.114 wherein the salt is a pharmaceutically acceptable salt.

Definitions

In this application, the following definitions apply, unless indicated otherwise.

The term "treatment", in relation to the uses of the compounds of the formula (1) or formula (1a), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" (as in "$C_{1-10}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" aryl, heteroaryl and "cycloalkenyl" are used in their conventional sense (e.g. as defined in the IUPAC Gold Book) unless indicated otherwise.

The term "saturated hydrocarbon group" as in "$C_{1-4}$ saturated hydrocarbon group" refers to a hydrocarbon group containing no carbon-carbon double bonds or triple bonds. The saturated hydrocarbon group can therefore be an alkyl group, a cycloalkyl group, a cycloalkylalkyl group, an alkylcycloalkyl group or a alkylcycloalkylalkyl group. Examples of $C_{1-4}$ saturated hydrocarbon groups include $C_{1-4}$ alkyl groups, cyclopropyl, cyclobutyl and cyclopropylmethyl.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^2$, $R^3$ and $R^4$ above, where stated, one or two but not all, carbon atoms of the non-aromatic hydrocarbon group may optionally be replaced by a heteroatom selected from O, N and S and (in the case of $R^1$ and $R^4$) oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—$S(O)_2$—$CH_2$—, replacement of a carbon atom in a —$CH_2$—$CH_2$—$CH_2$-chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) or formula (1a) can exist in the form of salts, for example acid addition salts or, in certain cases salts of organic and inorganic bases such as carboxylate, sulfonate and phosphate salts. All such salts are within the scope of this invention, and references to compounds of the formula (1) or formula (1a) include the salt forms of the compounds as defined in Embodiments 1.113 to 1.115.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.120) may be formed with a wide variety of acids, both inorganic and organic. Examples of acid addition salts falling within Embodiment 1.113 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) or formula (1a) contain an amine function, these may form quaternary ammonium salts, for example by reaction with an alkylating agent according to methods well known to the skilled person. Such quaternary ammonium compounds are within the scope of formula (1) or formula (1a) respectively.

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.121), the invention provides a geometric isomer of a compound according to any one of Embodiments 1.1 to 1.115.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.132) the invention provides a compound according to any one of Embodiments 1.1 to 1.121 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.133), the invention provides compositions containing a compound according to Embodiment 1.132 having one or more chiral centres, wherein at least 55% (e.g. at least 60%, 65%, 70%, 75%, 80%, 85%, 90% or 95%) of the compound of Embodiment 1.132 is present as a single optical isomer (e.g. enantiomer or diastereoisomer).

In one general embodiment (Embodiment 1.134), 99% or more (e.g. substantially all) of the total amount of the compound (or compound for use) of Embodiment 1.132 is present as a single optical isomer.

For example, in one embodiment (Embodiment 1.135) the compound is present as a single enantiomer.

In another embodiment (Embodiment 1.136), the compound is present as a single diastereoisomer.

The invention also provides mixtures of optical isomers, which may be racemic or non-racemic. Thus, the invention provides:

1.136 A compound according to Embodiment 1.132 which is in the form of a racemic mixture of optical isomers.

1.137 A compound according to Embodiment 1.132 which is in the form of a non-racemic mixture of optical isomers.

Isotopes

The compounds of the invention as defined in any one of Embodiments 1.1 to 1.137 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.140), the compound of any one of Embodiments 1.1 to 1.137 contains no radioactive isotopes. Such compounds are preferred for therapeutic use.

In another embodiment (Embodiment 1.141), however, the compound of any one of Embodiments 1.1 to 1.137 may contain one or more radioisotopes. Compounds containing such radioisotopes may be useful in a diagnostic context.

Solvates

Compounds of the formula (1) or formula (1a) as defined in any one of Embodiments 1.1 to 1.141 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.150 and 1.151, the invention provides:

1.151 A compound according to any one of Embodiments 1.1 to 1.141 in the form of a solvate.

1.152 A compound according to Embodiment 1.151 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.153), the invention provides a compound as defined in any one of Embodiments 1.1 to 1.141 in an anhydrous form (e.g. anhydrous crystalline form).

Crystalline and Amorphous Forms

The compounds of any one of Embodiments 1.1 to 1.153 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.160 A compound according to any one of Embodiments 1.1 to 1.153 in a crystalline form.

1.161 A compound according to any one of Embodiments 1.1 to 1.153 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.162 A compound according to any one of Embodiments 1.1 to 1.153 which is in an amorphous form.

Prodrugs

The compounds of the formula (1) or formula (1a) as defined in any one of Embodiments 1.1 to 1.162 may be presented in the form of a pro-drug. By "prodrugs" is meant for example any compound that is converted in vivo into a biologically active compound of the formula (1) or formula (1a), as defined in any one of Embodiments 1.1 to 1.162.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.170), the invention provides a pro-drug of a compound as defined in any one of Embodiments 1.1 to 1.170 wherein the compound contains a functional group which is convertable under physiological conditions to form a hydroxyl group or amino group.

Complexes and Clathrates

Also encompassed by formula (1) or formula (1a) in Embodiments 1.1 to 1.170 are complexes (e.g. inclusion complexes or clathrates with compounds such as cyclodextrins, or complexes with metals) of the compounds of Embodiments 1.1 to 1.170.

Accordingly, in another embodiment (Embodiment 1.180), the invention provides a compound according to any one of Embodiments 1.1 to 1.170 in the form of a complex or clathrate.

Biological Activity and Therapeutic Uses

The compounds of the present invention have activity as muscarinic $M_1$ receptor agonists. The muscarinic activity of the compounds can be determined using the Phospho-ERK1/2 assay described in Example A below.

A significant advantage of compounds of the invention is that they are highly selective for the $M_1$ receptor relative to the $M_2$ and $M_3$ receptor subtypes. Compounds of the invention are not agonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention are also highly selective for the $M_4$ receptor relative to the $M_1$ receptor. Examples of such compounds include the compound of Example 2-11 (Isomer 2).

Other compounds of the invention have activity at both the $M_1$ and $M_4$ receptors. Examples of such compounds include compounds of Examples 1 to 4 and 8 to 10.

Accordingly, in Embodiments 2.1 to 2.9, the invention provides:

2.1 A compound according to any one of Embodiments 1.1 to 1.180 for use in medicine.

2.2 A compound according to any one of Embodiments 1.1 to 1.180 for use as a muscarinic $M_1$ and/or $M_4$ receptor agonist.

2.3 A compound according to any one of Embodiments 1.1 to 1.180 which is a muscarinic $M_1$ receptor agonist having a $pEC_{50}$ in the range from 6.0 to 8.5 and an $E_{max}$ of at least 90 against the $M_1$ receptor in the assay of Example A herein or an assay substantially similar thereto.

2.4 A compound according to Embodiment 2.3 which is a muscarinic $M_1$ receptor agonist having a $pEC_{50}$ in the range from 6.5 to 7.5.

2.5 A compound according to Embodiment 2.3 or Embodiment 2.4 having an $E_{max}$ of at least 95 against the $M_1$ receptor.

2.6 A compound according to any one of Embodiments 1.1 to 1.180 which is a muscarinic $M_4$ receptor agonist having a $pEC_{50}$ in the range from 6.0 to 9.1 and an $E_{max}$ of at least 90 against the $M_4$ receptor in the assay of Example A herein or an assay substantially similar thereto.

2.7 A compound according to Embodiment 2.6 which is a muscarinic $M_4$ receptor agonist having a $pEC_{50}$ in the range from 6.5 to 8.0.

2.8 A compound according to Embodiment 2.6 or Embodiment 2.7 having an $E_{max}$ of at least 95 against the $M_4$ receptor.

2.9 A compound according to any one of Embodiments 2.3 to 2.8 which is selective for the $M_1$ and/or $M_4$ receptor compared to the muscarinic $M_2$ and $M_3$ receptors.

2.10 A compound according to Embodiment 2.9 which is selective for the $M_1$ receptor compared to the muscarinic $M_2$ and $M_3$ receptors.

2.11 A compound according to Embodiment 2.9 which is selective for the $M_4$ receptor compared to the muscarinic $M_2$ and $M_3$ receptors.

2.12 A compound according to any one of Embodiments 2.3 to 2.5 which is selective for the $M_1$ receptor compared to the muscarinic $M_2$, $M_3$ and $M_4$ receptors.

2.13 A compound according to any one of Embodiments 2.6 to 2.8 which is selective for the $M_4$ receptor compared to the muscarinic $M_1$, $M_2$ and $M_3$ receptors.

2.14 A compound according to any one of Embodiments 2.3 to 2.8 which is selective for the $M_1$ and $M_4$ receptor compared to the muscarinic $M_2$ and $M_3$ receptors.

2.15 A compound according to any one of Embodiments 2.3 to 2.14 which has a $pEC_{50}$ of less than 5 and an $E_{max}$ of less than 50 against the muscarinic $M_2$ and $M_3$ receptor subtypes.

2.16 A compound according to Embodiment 2.15 which has a $pEC_{50}$ of less than 4.5 and/or an $E_{max}$ of less than 30 against the muscarinic $M_2$ and $M_3$ receptor subtypes.

2.17 A compound according to any one of Embodiments 1.1 to 1.180 and Embodiments 2.3 to 2.16 for use in the treatment of a disease or condition mediated by the muscarinic $M_1$ receptor.

By virtue of their muscarinic $M_1$ and/or $M_4$ receptor agonist activity, compounds of the invention can be used in the treatment of Alzeimer's disease, schizophrenia and other psychotic disorders, cognitive disorders and other diseases mediated by the muscarinic $M_1$ and/or $M_4$ receptor, and can also be used in the treatment of various types of pain.

Accordingly, in Embodiments 2.18 to 2.35, the invention provides:

2.18 A compound according to any one of Embodiments 1.1 to 1.180 for use in the treatment of a cognitive disorder or psychotic disorder.

2.19 A compound for use in according to Embodiment 2.18 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders, epilepsy and schizo-affective disorder.

2.20 A compound according to any one of Embodiments 1.1 to 1.180 for use in the treatment of Alzheimer's disease.

2.21 A compound according to any one of Embodiments 1.1 to 1.180 for use in the treatment of Schizophrenia.

2.22 A compound according to any one of Embodiments 1.1 to 1.180 for use in the treatment of Alzheimer's disease and/or dementia with Lewy bodies.

2.23 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.180.

2.24 A method according to Embodiment 2.20 wherein the cognitive disorder comprises, arises from or is associated with a condition as defined in Embodiment 2.19.

2.25 A method according to Embodiment 2.24 wherein the cognitive disorder arises from or is associated with Alzheimer's disease.

2.26 A method according to Embodiment 2.24 wherein the cognitive disorder is Schizophrenia.

2.27 The use of a compound according to any one of Embodiments 1.1 to 1.180 for the manufacture of a medicament for the treatment of a cognitive disorder.

2.28 The use according to Embodiment 2.27 wherein the cognitive disorder comprises, arises from or is associated with a condition as defined in Embodiment 2.11.

2.29 The use according to Embodiment 2.28 wherein the cognitive disorder arises from or is associated with Alzheimer's disease.

2.30 The use according to Embodiment 2.28 wherein the cognitive disorder is Schizophrenia.

2.31 A compound according to any one of Embodiments 1.1 to 1.180 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherapeutic neuralgia, diabetic neuropathy, radicular pain, sciatica, back pain, head or neck pain, severe or intractable pain, nociceptive pain, breakthrough pain, post-surgical pain, or cancer pain.

2.32 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherapeutic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.180.

2.33 A compound according to any one of Embodiments 1.1 to 1.180 for the treatment of peripheral disorders such as reduction of intra ocular pressure in Glaucoma and treatment of dry eyes and dry mouth including Sjogren's Syndrome.

2.34 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.180.

2.35 The use of a compound according to any one of Embodiments 1.1 to 1.180 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherapeutic neuralgia, diabetic neuropathy, radicular pain, sciatica, back pain, head or neck pain, severe or intractable pain, nociceptive pain, breakthrough pain, postsurgical pain, or cancer pain or for the treatment of peripheral disorders such as reduction of intra ocular pressure in Glaucoma and treatment of dry eyes and dry mouth including Sjogren's Syndrome.

Methods for the Preparation of Compounds of the Formula (1) and Formula (1a)

Compounds of the formula (1) and formula (1a) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.180, which process comprises:

(A) the reaction of a compound of the formula (10) or (10a)

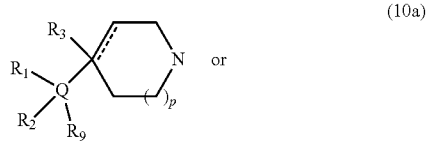

with a compound of the formula (11):

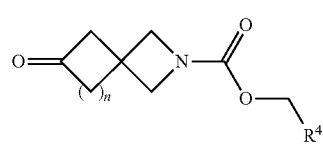

under reductive amination conditions; wherein $R^1$, $R^2$, $R^3$, $R^9$, $R^4$ and Q are as defined in any one of Embodiments 1.1 to 1.180; or (B) the reaction of a compound of the formula (12) or (12a):

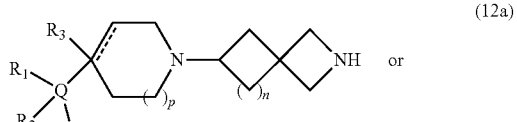

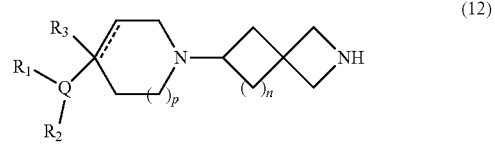

with a compound of the formula Cl—C(=O)—CH$_2$—R$^4$, in the presence of a base; or (C) the reaction of a compound of the formula (10) or (10a)

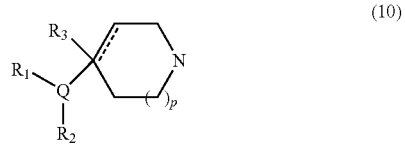

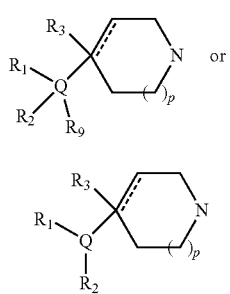

with a compound of the formula (13):

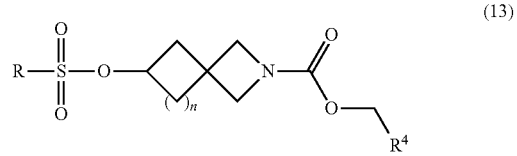

under nucleophilic substitution conditions; wherein $R^1$, $R^2$, $R^3$, $R^9$, $R^4$ and Q are as defined in any one of Embodiments 1.1 to 1.180; and optionally:

(D) converting one compound of the formula (1) or formula (1a) to another compound of the formula (1) or formula (1a) respectively.

In process variant (A), the piperidine heterocycle (10) or (10a) is reacted with the substituted ketone (11) under reductive amination conditions. The reductive amination reaction is typically carried out at ambient temperature using a borohydride reducing agent such as sodium triacetoxyborohydride in a solvent such as dichloromethane or dichloroethane containing acetic acid.

In process variant (C), the piperidine heterocycle (10) or (10a) is reacted with the sulfonic ester (13, R=methyl, trifluoromethyl or 4-methylphenyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide.

Intermediate compounds of the formula (12) and (12a) can be prepared by the series of reactions shown in Scheme 1 and Scheme 1a respectively below.

Scheme 1a

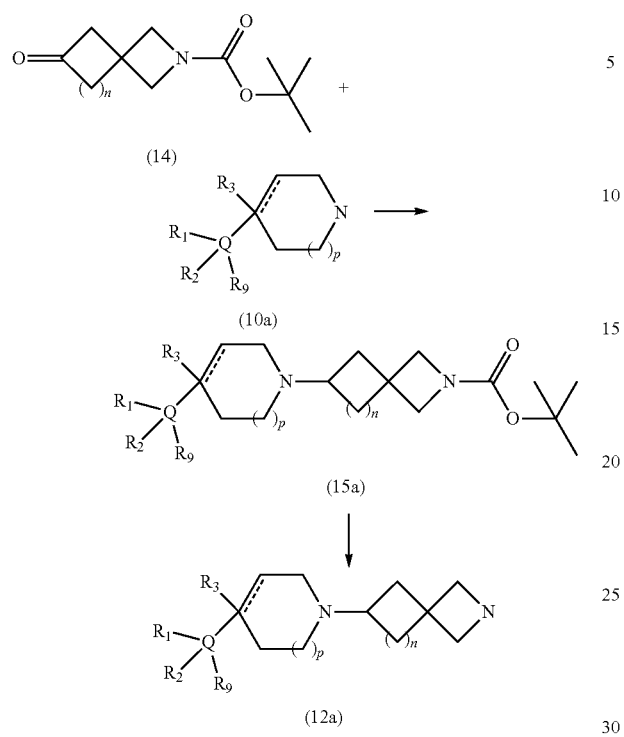

Scheme 1

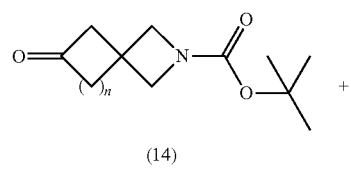

In reaction Scheme 1 or Scheme 1a, the piperidine heterocycle (10) or (10a) respectively is reacted with the Boc-protected spiroketone (14) under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate piperidine compound (15) or (15a) respectively which is then deprotected by removal of the Boc group by treatment with acid (e.g. trifluoroacetic acid in dichloromethane) to give the compound (12) or (12a) respectively.

Compounds of the formula (12) or (12a) can also be prepared by the sequence of reactions shown in Scheme 2 or Scheme 2a respectively below.

Scheme 2a

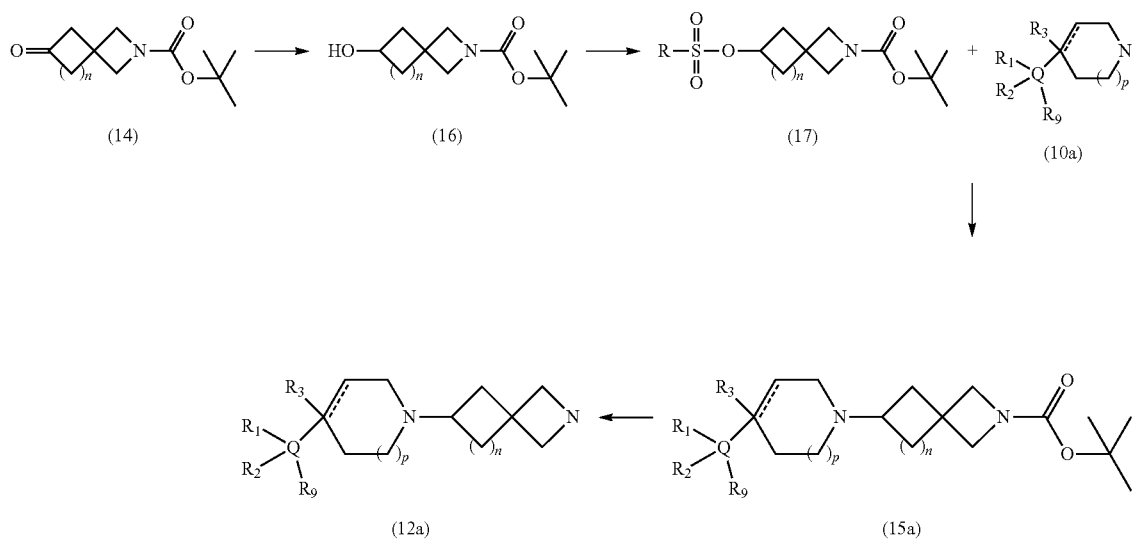

Scheme 2

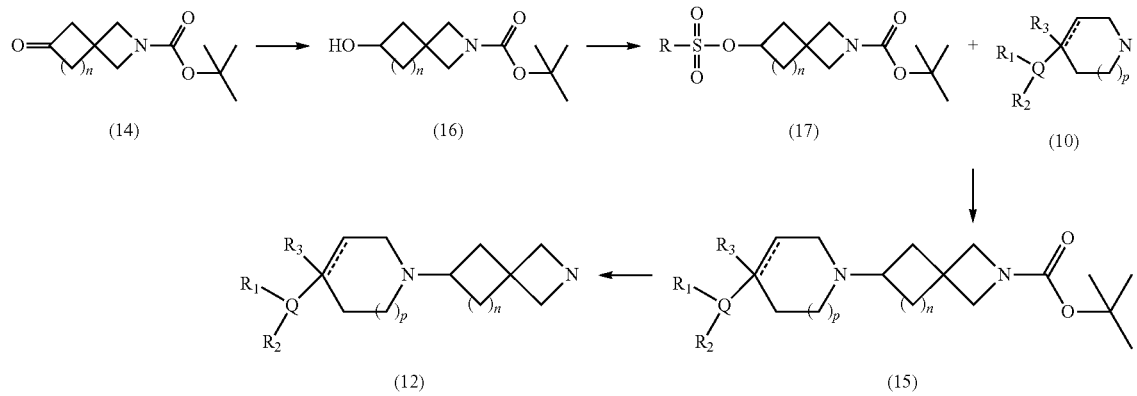

In Scheme 2 or Scheme 2a, the Boc-protected spiroketone (14) is reduced to the alcohol (16) using sodium borohydride in methanol. The alcohol (16) is then activated as the sulfonic ester (17, R=methyl, trifluoromethyl or 4-methylphenyl) using the corresponding sulfonyl chloride in dichloromethane in the presence of a tertiary amine such as triethylamine or N,N-diisopropylethylamine. The sulfonic ester (17) is reacted with the piperidine heterocycle (10) or (10a) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide to give compound (15) or (15a) respectively which is then deprotected by removal of the Boc group by treatment with acid (e.g. trifluoroacetic acid in dichloromethane) to give the compound (12) or (12a) respectively.

Once formed, one compound of the formula (1) or formula (1a), or a protected derivative thereof, can be converted into another compound of the formula (1) or formula (1a) respectively by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis,* Volumes 1-17, John Wiley, edited by Mary Fieser (ISBN: 0-471-58283-2). Examples of these transformations include amide bond formation, urea formation, carbamate formation, alkylation reactions, N-arylation reaction and C—C bond coupling reactions.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) or formula (1a) as defined in any one of Embodiments 1.1 to 1.180 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) or formula (1a) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient.

Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) or formula (1a) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 2-12

The compounds of Examples 1-1 to 2-12 shown in Table 1 below have been prepared. Their NMR and LCMS properties and the methods used to prepare them are set out in Table 3.

TABLE 1

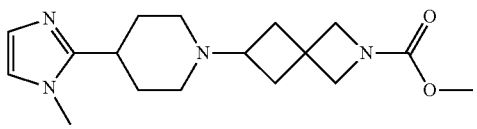 [SMILES: COC(=O)N1CC2(CC(N3CCC(c4nccn4C)CC3)C2)C1]

Example 1-1

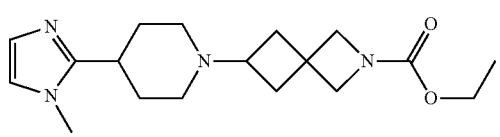

Example 1-2

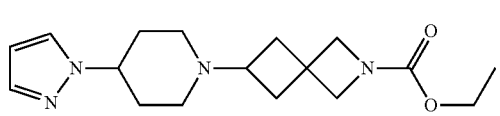 [SMILES: CCOC(=O)N1CC2(CC(N3CCC(n4cccn4)CC3)C2)C1]

Example 1-3

TABLE 1-continued
| | |
|---|---|
| 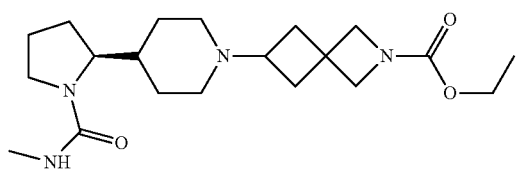 [SMILES: CCOC(=O)N1CC2(CC(N3CCC([C@@H]4CCCN4C(=O)NC)CC3)C2)C1] | Example 1-4 |
| 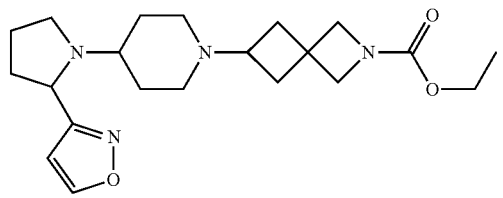 [SMILES: CCOC(=O)N1CC2(CC(N3CCC(N4CCCC4c4ccon4)CC3)C2)C1] | Example 1-5 |
| 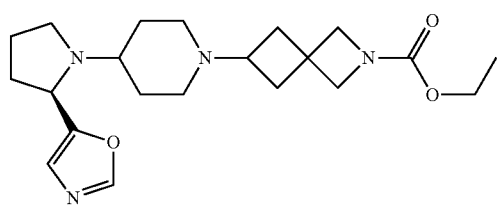 [SMILES: CCOC(=O)N1CC2(CC(N3CCC(N4CCC[C@@H]4c4cnco4)CC3)C2)C1] | Example 1-6 |
| 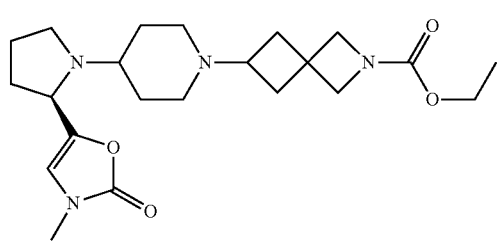 [SMILES: CCOC(=O)N1CC2(CC(N3CCC(N4CCC[C@@H]4c4cn(C)c(=O)o4)CC3)C2)C1] | Example 1-7 |
| 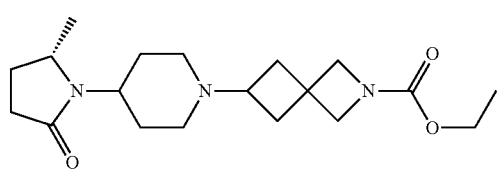 [SMILES: CCOC(=O)N1CC2(CC(N3CCC(N4C(=O)CC[C@@H]4C)CC3)C2)C1] | Example 1-8 |
| 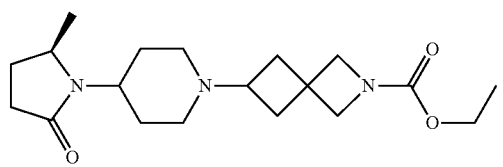 [SMILES: CCOC(=O)N1CC2(CC(N3CCC(N4C(=O)CC[C@H]4C)CC3)C2)C1] | Example 1-9 |
| 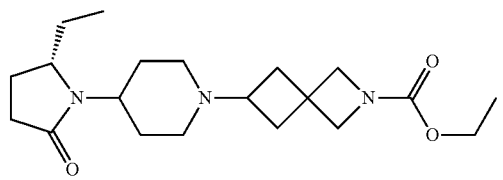 [SMILES: CCOC(=O)N1CC2(CC(N3CCC(N4C(=O)CC[C@@H]4CC)CC3)C2)C1] | Example 1-10 |
| 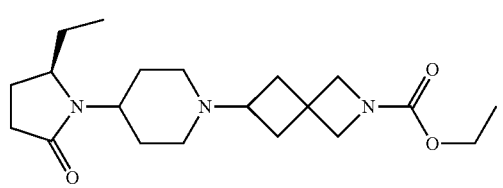 [SMILES: CCOC(=O)N1CC2(CC(N3CCC(N4C(=O)CC[C@H]4CC)CC3)C2)C1] | Example 1-11 |

TABLE 1-continued
| | |
|---|---|
| 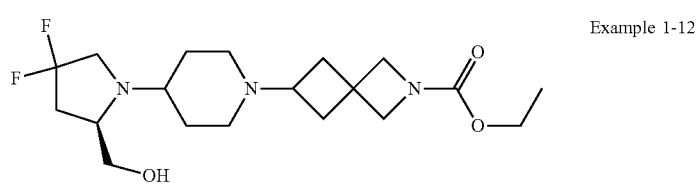 | Example 1-12 |
| 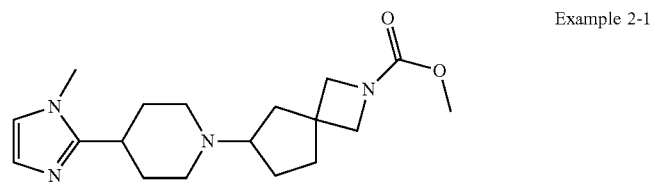 | Example 2-1 |
| 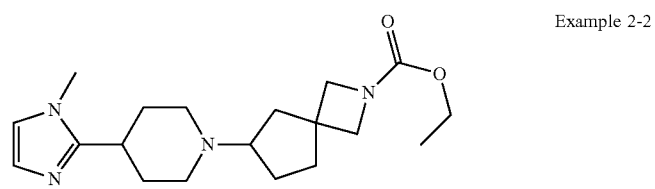 | Example 2-2 |
| 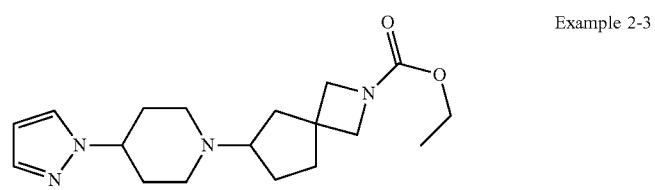 | Example 2-3 |
| 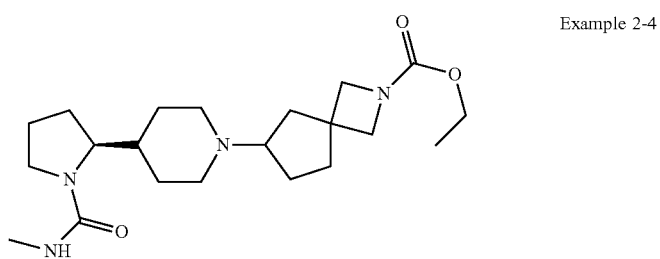 | Example 2-4 |
| 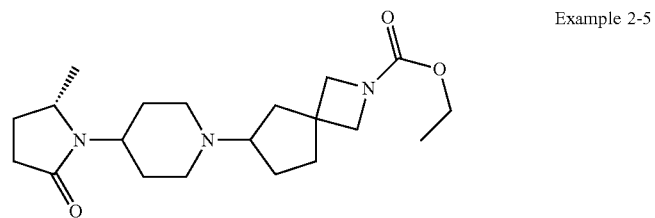 | Example 2-5 |
| 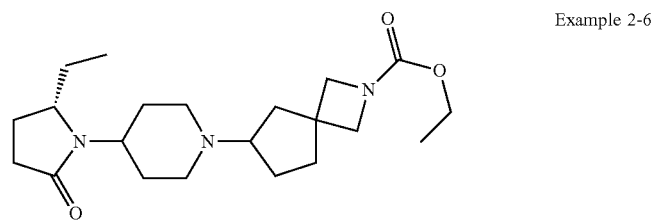 | Example 2-6 |

TABLE 1-continued

| | |
|---|---|
| 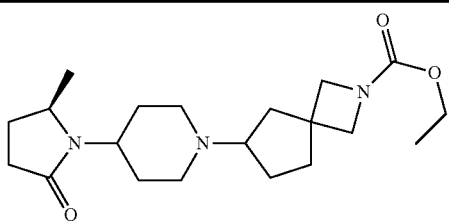 | Example 2-7 |
| 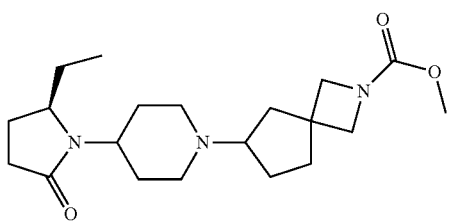 [SMILES: CC[C@@H]1CCC(=O)N1C1CCN(C2CCC3(C2)CN(C(=O)OC)C3)CC1] | Example 2-8 |
| 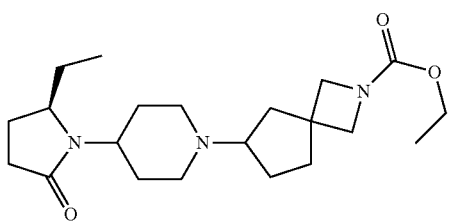 [SMILES: CCOC(=O)N1CC2(CCC(N3CCC(N4C(=O)CC[C@H]4CC)CC3)C2)C1] | Example 2-9 |
| 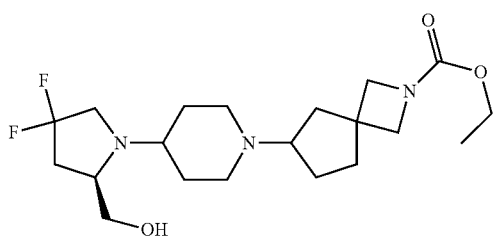 [SMILES: CCOC(=O)N1CC2(CCC(N3CCC(N4CC(F)(F)C[C@@H]4CO)CC3)C2)C1] | Example 2-10 |
| 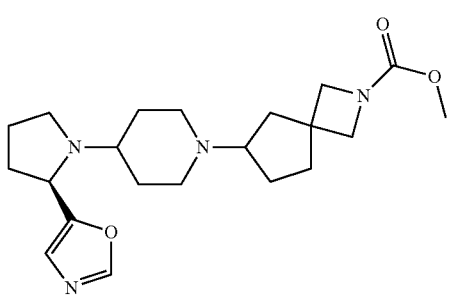 [SMILES: COC(=O)N1CC2(CCC(N3CCC(N4CCC[C@@H]4c4cnco4)CC3)C2)C1] | Example 2-11 |
| 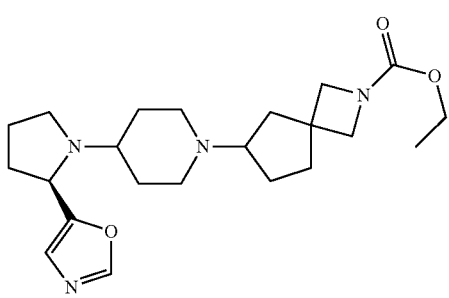 [SMILES: CCOC(=O)N1CC2(CCC(N3CCC(N4CCC[C@@H]4c4cnco4)CC3)C2)C1] | Example 2-12 |

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and Silica gel F254 (Merck) as a stationary phase. Microwave-mediated reactions were performed in Biotage Initiator or CEM Discover microwave reactors. LCMS experiments were typically carried out using electrospray conditions as specified for each compound under the following conditions:

LCMS Methods A and B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L $H_2O$+2.5 mL ammonia solution; solvent D=2.5 L MeCN+135 mL $H_2O$+2.5 mL ammonia solution); Injection volume 3 μL; UV detection 230 to 400 nM; column temperature 45° C.; Flow rate 1.5 mL/min.

LCMS Method C

Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/5, 2.00/95, 2.50/95, 2.60/5, 3.00/5; Solvents: solvent A=2.5 L $H_2O$+2.5 mL of (28% $NH_3$ in $H_2O$); solvent B=2.5 L MeCN+130 mL $H_2O$+2.5 mL of (28% $NH_3$ in $H_2O$); Injection volume 0.5 μL; UV detection 190 to 400 nM; column temperature 40° C.; Flow rate 1.5 mL/min.

LCMS Methods D and E

Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method D: 0.00/2, 0.10/2, 2.50/95, 3.50/95, 3.55/2, 4.00/2 or Method E: 0.00/2, 0.10/2, 8.40/95, 9.40/95, 9.50/2, 10.00/2; Solvents: solvent C=2.5 L $H_2O$+2.5 mL 28% ammonia in $H_2O$ solution; solvent D=2.5 L MeCN+135 mL $H_2O$+2.5 mL 28% ammonia in $H_2O$ solution); Injection volume 1 μL; UV detection 230 to 400 nM; Mass detection 130 to 800 AMU (+ve and −ve electrospray); column temperature 45° C.; Flow rate 1.5 mL/min.

LCMS Method F

Instruments: Waters 2695, Photo Diode Array, ZQ-2000 Detector; Column: X-Bridge C18, 3.5 micron, 150×4.6 mm; Gradient [time (min)/solvent B in A (%)]: 0.00/5, 5.00/90, 5.80/95, 10/95; Solvents: solvent A=0.1% ammonia in $H_2O$; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method G

Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/2, 0.10/2, 8.40/95, 10.00/95; Solvents: solvent A=2.5 L $H_2O$+2.5 mL of (28% $NH_3$ in $H_2O$); solvent B=2.5 L MeCN+130 mL $H_2O$+2.5 mL of (28% $NH_3$ in $H_2O$); Injection volume 0.5 μL; UV detection 190 to 400 nM; column temperature 40° C.; Flow rate 1.5 mL/min.

LCMS data in the experimental section are given in the format: Mass ion, retention time, UV activity.

Abbreviations d=day(s)
DCE=dichloroethane
DCM=dichloromethane
DIPEA=diisopropylethylamine
DMF=dimethylformamide
DMSO=dimethylsulfoxide
ES=electro spray ionisation
EtOAc=ethyl acetate
h=hour(s)
HPLC=high performance liquid chromatography
LC=liquid chromatography
MeCN=acetonitrile
MeOH=methanol
min=minute(s)
MS=mass spectrometry
$Et_3N$=triethylamine
NMR=nuclear magnetic resonance
rt=room temperature
sat.=saturated
sol.=solution
STAB=sodium triacetoxyborohydride
THF=tetrahydrofuran
TLC=thin layer chromatography Prefixes n-, s-, i-, t- and tert- have their usual meanings: normal, secondary, iso, and tertiary.

Final compounds are named using the software package ACD/ChemSketch Version 12. Intermediates and reagents are named either using the software package ACD/ChemSketch Version 12 or are referred to using their common name as typically found in suppliers catalogues.

Synthesis of Intermediates

Route 1

Typical Procedure for the Preparation of Ketones, as Exemplified by the Preparation of Intermediate 2, ethyl 6-oxo-2-azaspiro[3.3]heptane-2-carboxylate

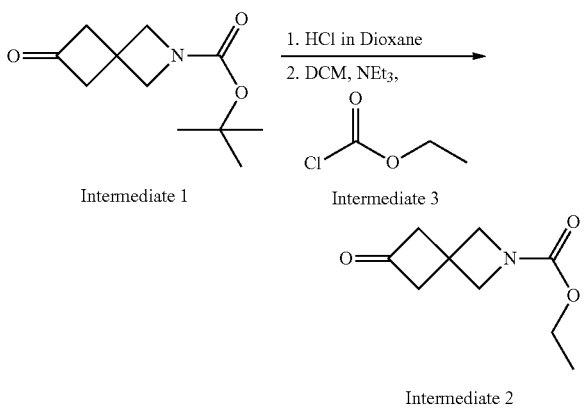

2-Boc-6-oxo-2-azaspiro[3.3]heptane (0.65 g, 3.08 mmol) was added portionwise to hydrogen chloride (4 M dioxane solution, 3.10 mL, 12.40 mmol). After 24 h, the reaction was concentrated in vacuo and the residual solid dissolved in a mixture of Et$_3$N (0.86 mL, 6.15 mmol) and DCM (13.5 mL). On completion of dissolution the solution was immediately cooled to 0° C., then ethyl chloroformate (0.32 mL, 3.38 mmol) was added dropwise. After 18 h, the mixture was poured into DCM (50 mL) and NaHCO$_3$ solution (50 mL) and extracted (2×50 mL). The organic layers were combined, washed with brine (10 mL), then dried over MgSO$_4$. The solvents were removed in vacuo, and the residue was purified by column chromatography (normal phase, [Biotage SNAP cartridge KP-sil 25 g, 40-63 μm, 60 Å, 50 mL per min, gradient 1 to 10% MeOH in DCM]) to provide ethyl 6-oxo-2-azaspiro[3.3]heptane-2-carboxylate, Intermediate 2, as a colourless oil which solidified to needles on standing (0.17 g, 30%).

The data for Intermediate 2 are in Table 2

Route 2

Typical Procedure for the Preparation of Pyrrolidin-2-Ones, as Exemplified by the Preparation of Intermediate 18, (S)-5-methylpyrrolidin-2-one

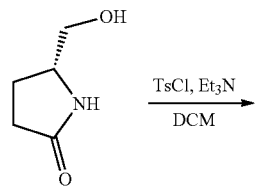

Intermediate 12

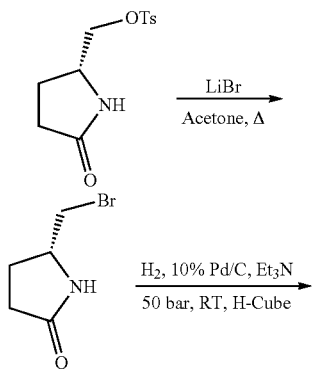

Intermediate 18

To a solution of (5R)-5-(hydroxymethyl)pyrrolidin-2-one (5.0 g, 43.4 mmol) in DCM (50 mL) was added triethylamine (7.7 mL, 55.5 mmol) and the mixture stirred at 0-5° C. for 10 min. To the mixture was added tosyl chloride (9.9 g, 51.9 mol) portionwise at 0-5° C. over 10 min and ZnCl$_2$ (0.1 g, 0.7 mmol) and the reaction mixture stirred at rt for 7 h. The solvents were removed in vacuo and the residue partitioned between H$_2$O (250 mL) and DCM (200 mL). The aqueous layer was extracted with DCM (2×200 mL), combined organics dried (Na$_2$SO$_4$) and the solvent removed in vacuo. The residue was purified by column chromatography (normal basic activated alumina, at 0 to 2.5% MeOH in DCM) to give (R)-(5-oxopyrrolidin-2-yl)methyl 4-methylbenzenesulfonate (5.3 g, 45%) as a white solid.

LCMS (Method F): m/z 270 (M+H)$^+$ (ES$^+$), at 3.44 min, UV active.

To a solution of (R)-(5-oxopyrrolidin-2-yl)methyl 4-methylbenzenesulfonate (5.0 g, 18.5 mmol) in acetone (10 mL) was added lithium bromide (4.8 g, 55.6 mmol) and the reaction mixture stirred at 80° C. overnight. The solvent was then removed in vacuo and the reaction mixture partitioned between H$_2$O (50 mL) and EtOAc (100 mL). The aqueous layer was extracted with EtOAc (2×100 mL), combined organics dried (Na$_2$SO$_4$), the solvent removed in vacuo and the residue purified by column chromatography (normal basic activated alumina, at 0.2 to 1.0% MeOH in DCM) to give (R)-5-(bromomethyl)pyrrolidin-2-one (3.0 g, 90%) as a light yellow liquid.

LCMS (Method F): m/z 178/180 (M+H)$^+$ (ES$^+$), at 2.24 min, UV active.

To (R)-5-(bromomethyl)pyrrolidin-2-one (3.0 g, 30 mmol) as a solution in MeOH (50 mL) was added Pd/C (0.3 g) and triethylamine (7.0 mL, 50 mmol) and 1166 psi H$_2$ (g) pressure was applied at 60° C. overnight in an autoclave. The reaction was filtered and the solvent removed from the filtrate in vacuo. The residue was purified by column chromatography (normal basic activated alumina, at 1.0 to 5.0% MeOH in DCM) to give Intermediate 18, (S)-5-methylpyrrolidin-2-one (1.0 g, 60%) as a light yellow liquid.

The data for Intermediate 18 are in Table 2

Route 3

Typical Procedure for the Preparation of Piperidines, as Exemplified by the Preparation of Intermediate 11, (5S)-5-methyl-1-(piperidin-4-yl)pyrrolidin-2-one

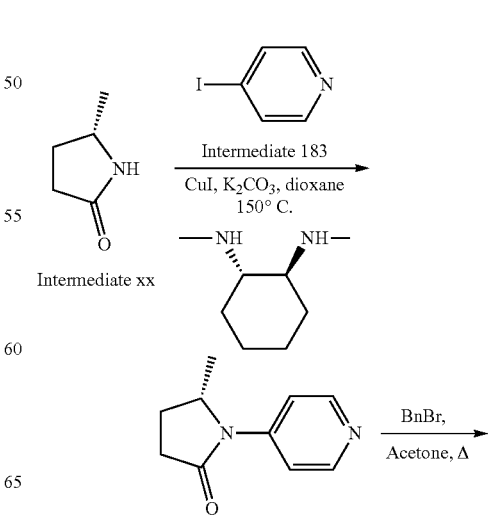

Intermediate xx

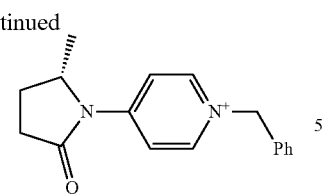

1. NaBH₄
   EtOH/H₂O
2. H₂, Pd/C
   EtOAc

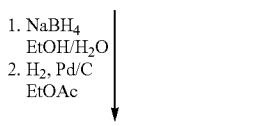

Intermediate 11

(S)-5-methylpyrrolidin-2-one (100 mg, 1.0 mmol), 4-iodo pyridine (255 mg, 1.0 mmol), K₂CO₃ (410 mg, 3.0 mmol), copper iodide (38 mg, 0.2 mmol) and trans-N,N'-dimethyl-cyclohexane-1,2-diamine (43 mg, 0.2 mmol) were dissolved in dioxane (10 mL) and the reaction mixture stirred at 150° C. for 18 h. The solvent was then removed in vacuo and the residue partitioned between H₂O (100 mL) and EtOAc (80 mL). The aqueous layer was extracted with EtOAc (2×80 mL), combined organics dried (Na₂SO₄) and the solvent removed in vacuo. The residue was purified by column chromatography (normal basic activated alumina, at 1.0 to 5.0% MeOH in DCM) to give (S)-5-methyl-1-(pyridin-4-yl)pyrrolidin-2-one (100 mg, 60%) as a light yellow solid.

LCMS (Method F): m/z 177 (M+H)⁺ (ES⁺), at 2.70 min, UV active.

To a solution of (S)-5-methyl-1-(pyridin-4-yl)pyrrolidin-2-one (200 mg, 1.1 mmol) in acetone (20 mL) was added benzyl bromide (210 mg, 1.2 mmol) and the reaction mixture stirred at 80° C. for 18 h. The solvent was then removed in vacuo to give (S)-1-benzyl-4-(2-methyl-5-oxopyrrolidin-1-yl)pyridin-1-ium (200 mg, 69%) as a light yellow solid which was taken on crude directly to the next step.

To a solution of (S)-1-benzyl-4-(2-methyl-5-oxopyrrolidin-1-yl)pyridin-1-ium (400 mg, 1.5 mmol) in ethanol/water (10 mL, 1:1) was added NaBH₄ (330 mg, 9.0 mmol) and the reaction mixture stirred at rt for 18 h. The solvent was then removed in vacuo, and the residue partitioned between H₂O (100 mL) and EtOAc (80 mL). The aqueous layer was extracted with EtOAc (2×80 mL), combined organics dried (Na₂SO₄) and the solvent removed in vacuo. The residue was purified column chromatography (normal basic activated alumina, at 1.0 to 5.0% MeOH in DCM) to give (S)-1-(1-benzyl-1,2,3,6-tetrahydropyridin-4-yl)-5-methylpyrrolidin-2-one (130 mg, 30%) as a light yellow solid.

LCMS (Method F): m/z 271 (M+H)⁺ (ES⁺), at 4.04 min, UV active.

To (S)-1-(1-benzyl-1,2,3,6-tetrahydropyridin-4-yl)-5-methylpyrrolidin-2-one (100 mg, 0.4 mmol) in EtOAc (10 mL) was added Pd/C (50 mg) and 569 psi H₂ (g) pressure applied overnight at 60° C. in an autoclave. The reaction mixture was filtered and the solvent removed from the filtrate in vacuo to give Intermediate 11, (S)-5-methyl-1-(piperidin-4-yl) pyrrolidin-2-one (42 mg, 62%) as a light yellow liquid.

The data for Intermediate 11 are in Table 2

Route 4

Typical Procedure for the Preparation of pyrrolidin-2-Ones as Exemplified by the Preparation of Intermediate 22, (5R)-5-ethylpyrrolidin-2-one

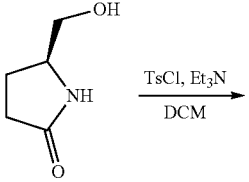

Intermediate 20

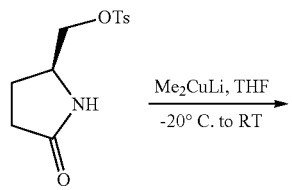

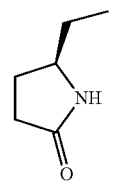

Intermediate 22

To a solution of (5S)-5-(hydroxymethyl)pyrrolidin-2-one (2.0 g, 17 mmol) and 4-methylbenzenesulfonyl chloride (5.3 g, 28 mmol) in DCM (24 mL) was added triethylamine (12 mL, 86 mmol). The resulting mixture was stirred at RT overnight then concentrated. The residue was dissolved in DCM and washed with 1 M aqueous HCl (×3) and brine (×1), then passed through a phase separator and concentrated to give a brown solid. The solid was recrystallized from DCM/isohexane to give a tan solid that was removed by filtration, washed with DCM/isohexane mixture and dried in air to give [(2S)-5-oxopyrrolidin-2-yl]methyl 4-methylbenzenesulfonate (3.13 g, 67%).

LCMS (Method C): m/z 270 (M+H)⁺ (ES⁺), at 0.97 min, UV active

Methyllithium (1.5 M in ether, 7.4 mL, 11 mmol) was added quickly with stirring to a suspension of copper iodide (1.06 g, 5.6 mmol) in THF (6 mL), pre-cooled in ice-water under N₂. The pale brown solution was stirred in ice-water for 45 min, then cooled to −20° C. A solution of [(2S)-5-oxopyrrolidin-2-yl]methyl 4-methylbenzenesulfonate (0.50 g, 1.9 mmol) in THF (6 mL) was added portion-wise over 2 min and the resulting solution was stirred at −20° C. for 45 min, then in ice-water overnight, allowing the cooling bath to slowly expire. The mixture was quenched with saturated aqueous NH₄Cl (15 mL) and stirred for several hours. The two-phase mixture was extracted with ether (×3), the organic phases were washed with brine, passed through a phase separator and concentrated to give Intermediate 22, crude (5R)-5-ethylpyrrolidin-2-one (0.124 g, 59%) as an oil.

The data for Intermediate 22 are in Table 2

Route 5

Procedure for the Preparation of Piperidines, as Exemplified by the Preparation of Intermediate 30, (R)-3-methyl-5-(1-(piperidin-4-yl)pyrrolidin-2-yl) oxazol-2(3H)-one trifluoroacetate salt

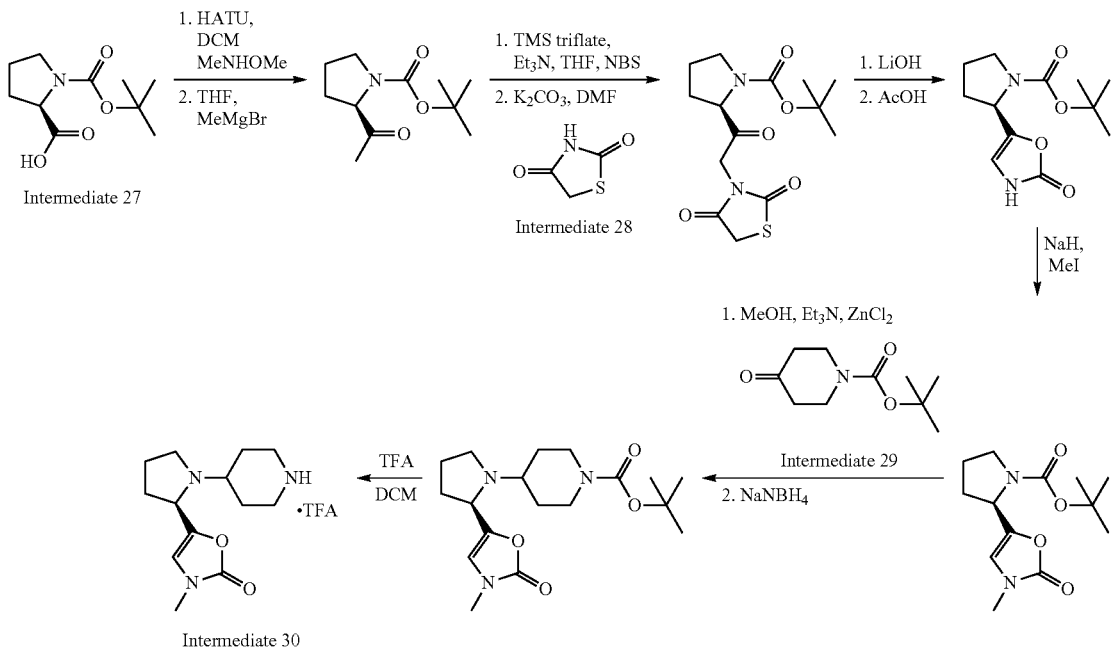

Intermediate 30

To a solution of (tert-butoxycarbonyl)-D-proline (10.0 g, 46.4 mmol) in DCM (100 mL) at 0° C. was added HATU (35.2 g, 92.8 mmol), the reaction mixture was stirred for 1 h at 0° C. N,O-dimethyl hydroxylamine (4.98 g, 46.4 mmol) and DIPEA (24.0 mL, 139 mmol) were added and the reaction mixture was stirred at rt for 16 h. The reaction mixture was partitioned between sat. NaHCO$_3$ solution (150 mL) and DCM (60 mL), the aqueous layer was further extracted with DCM (2×60 mL), the organic layers were combined, dried (Na$_2$SO$_4$) and solvents were removed in vacuo. The crude residue was purified by column chromatography (Silica, 0 to 30% EtOAc in Hexanes) to give tert-butyl (R)-2-(methoxy (methyl) carbamoyl) pyrrolidine-1-carboxylate (12.00 g, 100%) as a colourless gum.

LCMS (Method F): m/z 259 (M+H)$^+$ (ES$^+$), at 1.91 min, UV inactive

To a solution of tert-butyl (R)-2-(methoxy(methyl)carbamoyl)pyrrolidine-1-carboxylate (12.0 g, 46.4 mmol) in THF (120 mL) at −15° C., under nitrogen, methyl magnesium bromide (3.0 M Solution) (23.2 mL, 69.7 mmol) was added drop wise the reaction mixtures was stirred for at rt 3 h. The reaction mixture was partitioned between sat. NH$_4$Cl solution (60 mL) and EtOAc (30 mL), the aqueous layer was further extracted with EtOAc (2×30 mL), the organic layers were combined, dried (Na$_2$SO$_4$) and solvents were removed in vacuo. The residue was purified by column chromatography (Silica, 0 to 40% EtOAc in Hexanes) to give tert-butyl (R)-2-acetylpyrrolidine-1-carboxylate (9.75 g, 98.48%) as a yellow liquid.

LCMS (Method F): m/z 214 (M+H)$^+$ (ES$^+$), at 1.97 min, UV inactive

To a solution of tert-butyl (R)-2-acetylpyrrolidine-1-carboxylate (9.75 g, 45.0 mmol) in THF (20.0 mL) was added Et$_3$N (19.1 mL, 45.0 mmol) followed by trimethylsilyl trifluoromethanesulfonate (15.26 g, 68.6 mmol) drop wise at 0° C., the reaction mixture was stirred at 0° C. for 1 h. A solution of N-Bromo Succinimide (9.56 g, 54.0 mmol) in THF (50 mL) was added drop wise at 0° C. and the reaction mixtures was stirred at 0° C. for 30 min. The reaction mixture was partitioned between sat. NH$_4$Cl solution (150 mL) and EtOAc (70 mL), the aqueous layer was further extracted with EtOAc (2×70 mL), the organic layers were combined, dried (Na$_2$SO$_4$) and solvents were removed in vacuo. The residue was purified by column chromatography (Silica, 0 to 45% EtOAc in Hexanes) to give tert-butyl (R)-2-(2-bromoacetyl)pyrrolidine-1-carboxylate (4.00 g, 29.9%) as a yellow gum.

LCMS (Method F): m/z 292 (M+H)$^+$ (ES$^+$), at 2.12 min, UV inactive

To a solution of tert-butyl (R)-2-(2-bromoacetyl)pyrrolidine-1-carboxylate (4.00 g, 13.7 mmol) in DMF (15.0 mL) K$_2$CO$_3$ (2.84 g, 20.5 mmol) and thiazolidinedione (2.08 g, 17.8 mmol) were added and the reaction mixtures was stirred at rt for 3 h. The solvents were removed in vacuo, and the residue was partitioned between sat. NH$_4$Cl solution (100 mL) and EtOAc (50 mL), the aqueous layer was further extracted with EtOAc (2×50 mL), the organic layers were combined, dried (Na$_2$SO$_4$) and solvents were removed in vacuo. The residue was purified by column chromatography (Silica, 0 to 2% methanol in DCM) to give tert-butyl (R)-2-(2-(2,4-dioxothiazolidin-3-yl)acetyl)pyrrolidine-1-carboxylate (2.40 g, 53.45%) as a white solid.

LCMS (Method F): m/z 329 (M+H)$^+$ (ES$^+$), at 2.15 min, UV inactive

To a solution of tert-butyl (R)-2-(2-(2,4-dioxothiazolidin-3-yl)acetyl)pyrrolidine-1-carboxylate (2.40 g, 7.30 mmol) in dry THF (25.0 mL) was added LiOH (2 M in water) (875 mg) at 0° C., the reaction mixtures was stir at rt for 1 h. The reaction mixture was poured on to 5 mL acetic acid (5 mL) and then partitioned between H$_2$O (50 mL) and EtOAc (30 mL), the aqueous layer was further extracted with EtOAc (2×30 mL), the organic layers were combined, dried (Na$_2$SO$_4$) and solvents were removed in vacuo. The residue was purified by column chromatography (Silica, 0 to 3% methanol in DCM) to give tert-butyl (R)-2-(2-oxo-2,3-dihydrooxazol-5-yl)pyrrolidine-1-carboxylate (1.25 g, 67.20%) as a light yellow solid.

LCMS (Method F): m/z 255 (M+H)$^+$ (ES$^+$), at 1.91 min, UV inactive

To a solution of tert-butyl (R)-2-(2-oxo-2,3-dihydrooxazol-5-yl)pyrrolidine-1-carboxylate (1.5 g, 5.89 mmol) in DMF (30.0 mL) was added NaH (60%) (0.71 g, 17.7 mmol) at 0° C. under nitrogen, the reaction mixture was stirred at 0° C. for 30 min. Methyl iodide (1.25 g, 8.85 mmol) was added drop wise at 0-10° C. and the reaction mixture was stirred at rt for 30 min. The reaction mixture was partitioned between sat. NH$_4$Cl solution (50 mL) and EtOAc (40 mL), the aqueous layer was further extracted with EtOAc (2×40 mL), the organic layers were combined, dried (Na$_2$SO$_4$) and solvents were removed in vacuo. The residue was purified by column chromatography (Silica, 0 to 2% methanol in DCM) to give tert-butyl (R)-2-(3-methyl-2-oxo-2,3-dihydrooxazol-5-yl)pyrrolidine-1-carboxylate (1.50 g, 94.94%) as a colourless gum.

LCMS (Method F): m/z 213 (M+H)$^+$ (ES$^+$), at 2.01 min, UV inactive

To a solution of tert-butyl (R)-2-(3-methyl-2-oxo-2,3-dihydrooxazol-5-yl)pyrrolidine-1-carboxylate (1.50 g, 5.59 mmol) in DCM (10.0 mL) under nitrogen was added TFA (5.00 mL), the reaction mixtures was stirred at rt for 3 h. Toluene (10.0 mL) was added and solvents were removed in vacuo, the residue was azeotroped with toluene (2×10 mL) to give (R)-5-(pyrrolidin-2-yl)oxazol-2(3H)-one (897 mg, 95.43%) as a colourless gum.

LCMS (Method H): m/z 169 (M+H)$^+$ (ES$^+$), at 2.21 min, UV inactive

To a solution of tert-butyl (R)-5-(pyrrolidin-2-yl)oxazol-2(3H)-one (897 mg, 5.33 mmol) in methanol (20.0 mL) under nitrogen was added tert-butyl 4-oxopiperidine-1-carboxylate (1.06 g, 5.33 mmol), Et$_3$N (2.23 mL, 16.0 mmol) and zinc chloride (0.26 mL, 0.26 mmol), the reaction mixtures was stirred at 50-60° C. for 16 h. NaCNBH$_3$ (1.00 g, 16.0 mmol) was added portionwise at 0-10° C. and the reaction mixtures was stirred at rt for 6 h. The reaction mixture was partitioned between H$_2$O (50 mL) and EtOAc (35 mL), the aqueous layer was further extracted with EtOAc (2×30 mL), the organic layers were combined, dried (Na$_2$SO$_4$) and solvents were removed in vacuo. The residue was purified by column chromatography (Silica, 0 to 5% methanol in DCM) to give tert-butyl (R)-4-(2-(3-methyl-2-oxo-2,3-dihydrooxazol-5-yl)pyrrolidin-1-yl)piperidine-1-carboxylate (1.50 g, 80.04%) as a yellow gum.

LCMS (Method F): m/z 352 (M+H)$^+$ (ES$^+$), at 1.67 min, UV active

To a solution of tert-butyl (R)-4-(2-(3-methyl-2-oxo-2,3-dihydrooxazol-5-yl)pyrrolidin-1-yl)piperidine-1-carboxylate (1.50 g, 4.27 mmol) in DCM (20.0 mL) under nitrogen was added TFA (5.00 mL), the reaction mixtures was stirred at rt for 3 h. Toluene (10.0 mL) was added and solvents were removed in vacuo, the residue was azeotroped with toluene (2×10 mL) to give Intermediate 30, (R)-3-methyl-5-(1-(piperidin-4-yl)pyrrolidin-2-yl)oxazol-2(3H)-one.TFA (900 mg, 83.95%) as a brown gum.

The data for Intermediate 30 are in Table 2

Route 6

Procedure for the Preparation of Piperidines, as Exemplified by the Preparation of Intermediate 32, 4-[(2R)-4,4-difluoro-2-(hydroxymethyl)pyrrolidin-1-yl]piperidine trifluoroacetate salt

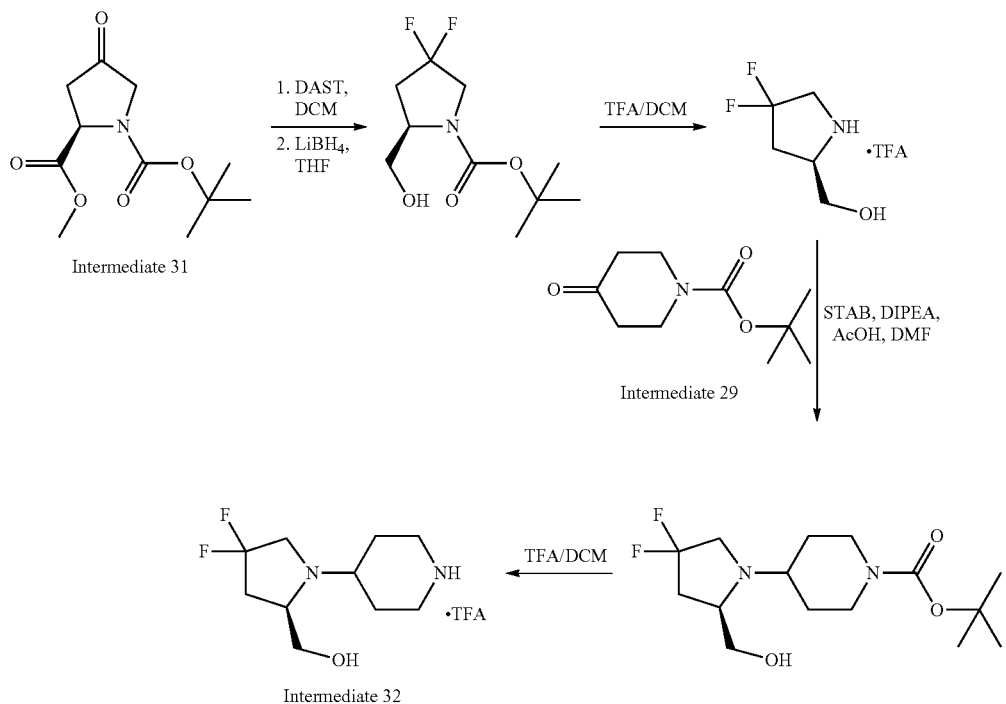

(R)-1-tert-Butyl 2-methyl 4-oxopyrrolidine-1,2-dicarboxylate (5.00 g, 20.5 mmol) was dissolved in DCM (15 mL) at −78° C. and DAST was added (8.1 mL, 30.8 mmol) dropwise. Reaction mixture was warmed to rt and stirred for 16 h. Reaction mixture diluted with DCM (100 mL) and washed with saturated NaHCO₃ (aq) (2×100 mL), combined aqueous layers washed with DCM (100 mL), the organic layers were combined, dried (Na₂SO₄) and solvents were removed in vacuo to give (R)-1-tert-Butyl 2-methyl 4,4-difluoropyrrolidine-1,2-dicarboxylate (5.34 g, 98%) as an yellow oil.

LCMS (Method F): m/z 210 (M+H−56)⁺ (ES⁺), at 2.17 min, UV inactive

To (R)-1-tert-Butyl 2-methyl 4,4-difluoropyrrolidine-1,2-dicarboxylate (5.34 g, 20.1 mmol) in THF (50 mL) was added lithium borohydride as a 3.0M solution in THF (13.4 mL, 40.3 mmol) at 0° C. and the reaction was warmed to RT and stirred for 3 h. The solvents were removed in vacuo, and the reaction mixture diluted with DCM (50 mL) and washed with sat. aqueous NaHCO₃ (2×50 mL), combined aqueous layers washed with DCM (50 mL), the organic layers were combined, dried (Na₂SO₄) and solvents were removed in vacuo. The residue was purified by column chromatography (Silica, 0 to 14% EtOAc in Hexane) to give tert-butyl (2R)-4,4-difluoro-2-(hydroxymethyl)pyrrolidine-1-carboxylate (4.3 g, 90%) as a yellow gum.

LCMS (Method F): m/z 186 (M+H−56)+(ES⁺), at 1.97 min, UV inactive

To a solution of tert-butyl (2R)-4,4-difluoro-2-(hydroxymethyl)pyrrolidine-1-carboxylate (3.8 g, 16.0 mmol) in DCM (20 mL) was added TFA (10 mL) the reaction mixtures was stirred at rt for 3 h. The solvents were removed in vacuo and the residue azeotroped with DCM (10 mL) and diethyl ether (10 mL) to give (2R)-4,4-difluoro-2-(hydroxymethyl)pyrrolidine trifluoroacetate salt (2.2 g, 100%) as a brown gum.

LCMS (Method I): m/z 138 (M+H)⁺ (ES⁺), at 3.78 min, UV inactive.

(2R)-4,4-difluoro-2-(hydroxymethyl)pyrrolidine trifluoroacetate salt (1.2 g, 8.7 mmol), tert-butyl 4-oxopiperidine-1-carboxylate (1.74 g, 8.7 mmol), triethylamine (6.1 mL, 43.7 mmol) and ZnCl₂ (1.0 M in ether) (0.4 mL, 0.43 mmol) were dissolved in MeOH (20 mL) and the reaction mixture stirred at 60° C. for 5 h. The mixture was cooled to 0° C. and NaCNBH₃ (1.65 g, 26.2 mmol) was added portionwise. The resulting reaction mixture was stirred at rt for 8 h. The solvents were removed in vacuo and the residue partitioned between H₂O (100 mL) and DCM (80 mL). The aqueous layer was extracted with DCM (2×80 mL) and combined organics were dried (Na₂SO₄) and the solvent were removed in vacuo. The residue was purified by column chromatography (Silica, 0 to 10% MeOH in DCM) to give tert-butyl 4-[(2R)-4,4-difluoro-2-(hydroxymethyl)pyrrolidin-1-yl]piperidine-1-carboxylate (2.5 g, 89%) as a yellow gum.

LCMS (Method I): m/z 265 (M+H−56)⁺ (ES⁺), at 4.08 min, UV inactive

A solution of tert-butyl 4-[(2R)-4,4-difluoro-2-(hydroxymethyl)pyrrolidin-1-yl]piperidine-1-carboxylate (2.5 g, 7.8 mmol) in DCM (20 mL) was added TFA (10 mL) the reaction mixtures was stirred at rt for 3 h. The solvents were removed in vacuo and the residue azeotroped with DCM (10 mL) and diethyl ether (10 mL) to give the crude Intermediate 32, 4-[(2R)-4,4-difluoro-2-(hydroxymethyl)pyrrolidin-1-yl]piperidine trifluoroacetate salt (1.71 g, 100%) as a brown gum.

The data for Intermediate 32 are in Table 2

Route 7

Procedure for the Preparation of Piperidines, as Exemplified by the Preparation of Intermediate 33, tert-butyl 4-[(2R)-2-(1,3-oxazol-5-yl)pyrrolidin-1-yl]piperidine-1-carboxylate

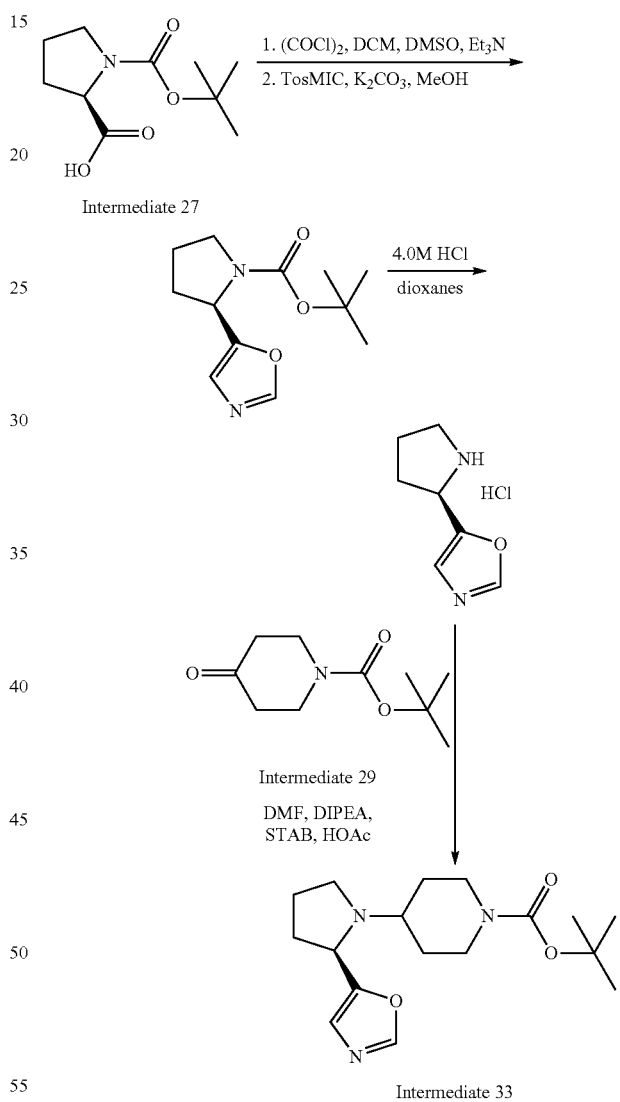

To a solution of oxalyl chloride (6.39 mL, 75 mmol) in DCM (200 mL) at −78° C., under nitrogen, was added DMSO (10.66 mL, 150 mmol) dropwise, the reaction mixture was stirred at −78° C. for 15 mins. (Tert-butoxycarbonyl)-D-proline (10.0 g, 46.4 mmol) in DCM (50 mL) was added dropwise to the reaction mixture at −78° C. over 1 h and then the reaction mixture was stirred at −78° C. for 15 mins. Et₃N (28 mL, 200 mmol) was added dropwise to the reaction mixture at −78° C., the reaction mixture was warmed to 0° C. and stirred for 1 h under nitrogen. The reaction mixture was quenched with saturated NaHCO₃ (aq) (200 mL), combined aqueous layers washed with DCM (100 mL), the organic layers were combined, dried (Na₂SO₄) and solvents were removed in vacuo to give crude tert-butyl (2R)-2-formylpyrrolidine-1-carboxylate (11.1 g, 100%) as a colourless oil. Used directly without further purification To a solution of crude tert-butyl (2R)-2-formylpyrrolidine-1-carboxylate (17.8 g, 89 mmol) in MeOH (300 mL) at 0° C., under nitrogen, was added K₂CO₃ (36.85 g, 267 mmol) followed by (p-Tolylsulfonyl)methyl isocyanide, TosMIC, (17.46 g, 89 mmol) portionwise over 10 mins. The reaction mixture was heated at 80° C. for 21 h under nitrogen, then cooled to rt over 16 h. The solvents were removed in vacuo and the residue was partitioned between DCM (100 mL) and ice-water (300 mL), the aqueous layer was further extracted with DCM (2×100 mL). The organic layers were combined and washed with brine (100 mL), dried by passing through a Biotage phase separator and the solvents were removed in vacuo. The residue was purified by column chromatography (Silica, 100% DCM) to give tert-butyl (2R)-2-(1,3-oxazol-5-yl)pyrrolidine-1-carboxylate (8.1 g, 38.0%) as a yellow oil.

LCMS (Method A): m/z 183 (M+H−56)+(ES⁺), at 1.07 min, UV inactive

Tert-butyl (2R)-2-(1,3-oxazol-5-yl)pyrrolidine-1-carboxylate (8.1 g, 34 mmol) was dissolved in 4 M HCl in dioxane (100 mL) and the reaction mixture stirred overnight at rt under N₂. The solvents were removed in vacuo to give 5-[(2R)-pyrrolidin-2-yl]-1,3-oxazole hydrochloride (5.9 g, 100%) as a yellow foam. Used directly without further purification To a solution of 5-[(2R)-pyrrolidin-2-yl]-1,3-oxazole hydrochloride (5.9 g, 34 mmol) and tert-butyl 4-oxopiperidine-1-carboxylate (6.71 g, 34 mmol) in DMF (150 mL) was added DIPEA (8.9 mL, 51 mmol) and the mixture stirred at 40° C. under N₂ for 2 h. The solution was cooled to rt, STAB (18.0 g, 85 mmol) and AcOH (1.95 mL, 34 mmol) were added and the reaction mixture was heated at 40° C. under N₂ for 72 h. The reaction mixture was cooled to rt and the solvents were removed in vacuo, the residue was carefully portioned between sat. aq. NaHCO₃ (200 mL) and DCM (100 mL), the aqueous layer was further extracted with DCM (3×100 mL). The organic layers were combined and washed with brine (100 mL), dried (MgSO₄) and solvents were removed in vacuo. The residue was purified by column chromatography (Silica, 0 to 10% MeOH in DCM) to give Intermediate 33, tert-butyl 4-[(2R)-2-(1,3-oxazol-5-yl)pyrrolidin-1-yl]piperidine-1-carboxylate (3.42 g, 31.5%) as a yellow oil.

The data for Intermediate 33 are in Table 2

Route 8

Procedure for the Preparation of Piperidines, as Exemplified by the Preparation of Intermediate 13, 4-[2-(1,2-oxazol-3-yl)pyrrolidin-1-yl]piperidine dihydrochloride

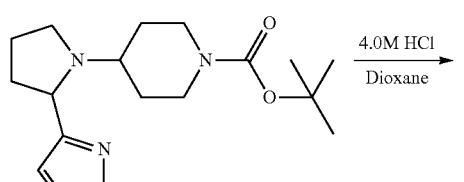

Intermediate 14

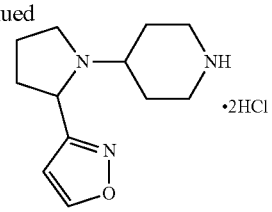

Intermediate 13

To tert-butyl 4-[2-(1,2-oxazol-3-yl)pyrrolidin-1-yl]piperidine-1-carboxylate (390 mg, 1.2 mmol) was added 4 M HCl in dioxane (4 mL) and the reaction mixture stirred overnight at rt under N₂. The mixture was then concentrated in vacuo to yield intermediate 13, 4-[2-(1,2-oxazol-3-yl)pyrrolidin-1-yl]piperidine dihydrochloride (330 mg, 92%) as a gum which solidified upon further azeotroping with DCM.

The data for Intermediate 13 are in Table 2

General Synthetic Procedures

Route a

Typical Procedure for the Preparation of Piperidines Via Sodium Triacetoxyborohydride Reductive Amination, Boc-Deprotection and Alkylcarbamate Formation as Exemplified by the Preparation of Example 1-2, Ethyl 6-[4-(1-methyl-1H-imidazol-2-yl)piperidin-1-yl]-2-azaspiro[3.3]heptane-2-carboxylate

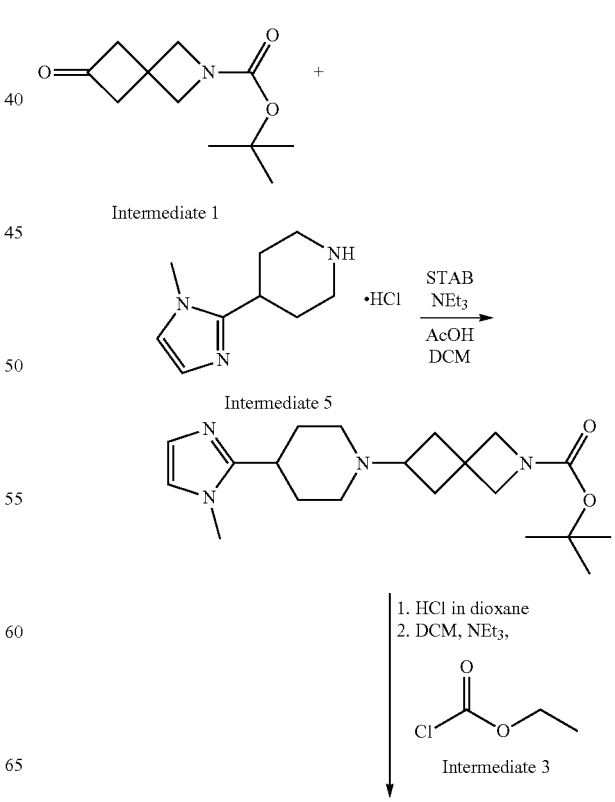

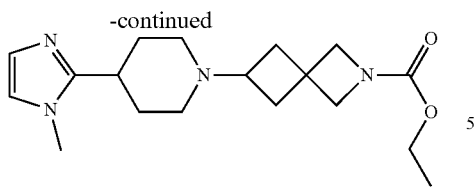

Example 1-2

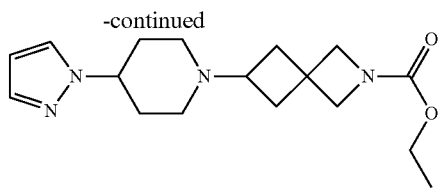

Example 1-3

4-(1-Methyl-1H-imidazol-2-yl-piperidine hydrochloride (0.303 g, 1.50 mmol) and 2-Boc-6-oxo-2-azaspiro[3.3]heptane (0.317 g, 1.50 mmol) were suspended in DCM (10 mL) at rt and triethylamine (0.42 mL, 3.0 mmol) was added. The reaction mixture was stirred at rt for 1 h, acetic acid (0.26 mL, 4.50 mmol) added stirred for 3 h. STAB (0.80 g, 3.75 mmol) was added and the reaction mixture was stirred overnight under nitrogen. The reaction mixture was quenched with the addition of sat. aqueous $NaHCO_3$ (15 mL) extracted with DCM (4×30 mL) and the solvents removed in vacuo. The residue was dissolved in DCM (15 mL), 4 M hydrogen chloride in dioxane (1.88 ml, 7.50 mmol) was added and the reaction mixture was stirred at rt for 18 h. The volatiles were then removed in vacuo and the residue dissolved in DCM (15 mL) and triethylamine (2.10 mL, 15.0 mmol). Ethyl chloroformate (214 μL, 2.25 mmol) was added dropwise and the solution stirred at rt for 18 h. The mixture was then poured into $NaHCO_{3(aq)}$ (40 ml) and DCM (40 ml), extracted with DCM (3×50 ml), and the combined DCM extracts washed concentrated in vacuo. The residue was purified by column chromatography (normal phase, [Biotage SNAP cartridge KP-sil 25 g, 40-63 μm, 60 Å, 50 mL per min, gradient 1% to 10% MeOH in DCM]). The residue was further purified by preparative reversed phase HPLC (Phenomenex Gemini-NX 5 μm C18 110A Axia column, 100×30 mm, eluting with 20 to 55% MeCN/Solvent B over 14.4 min at 30 mL/min [where solvent B is 0.2% of (28% $NH_3/H_2O$) in $H_2O$] and collecting fractions by monitoring at 205 nm) to give ethyl 6-[4-(1-methyl-1H-imidazol-2-yl)piperidin-1-yl]-2-azaspiro[3.3]heptane-2-carboxylate, Example 1-2 (60 mg, 12%), as a colourless solid.

The data for Example 1-2 are in Table 3.

Route b

Typical Procedure for the Preparation of Piperidines Via Sodium Triacetoxyborohydride Reductive Amination as Exemplified by the Preparation of Example 1-3, Ethyl 6-[4-(1H-pyrazol-1-yl)piperidin-1-yl]-2-azaspiro[3.3]heptane-2-carboxylate

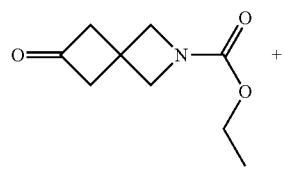

Intermediate 2

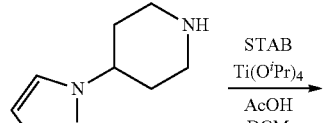

Intermediate 6

4-(1H-pyrazol-1-yl)piperidine (0.14 g, 0.93 mmol) and ethyl 6-oxo-2-azaspiro[3.3]heptane-2-carboxylate (0.17 g, 0.93 mmol) were dissolved in DCM (7.5 mL) at rt and titanium isopropoxide (0.55 mL, 1.02 mmol) was added. The reaction mixture was stirred at rt for 1 h. The reaction mixture was cooled to −5° C., then STAB (0.392 g, 1.852 mmol) and acetic acid (22 μL, 0.37 mmol) were added and the reaction mixture was stirred overnight under nitrogen while warming to rt. The reaction mixture was quenched with the addition of $NaHCO_3$ $_{(sat\ aq.)}$ (5 ml) and diluted with DCM (50 mL) then filtered through a pad of celite. The layers were separated and the aqueous layer was extracted with DCM (2×50 mL). The combined DCM layers were washed with brine (10 mL), then dried over $MgSO_4$. The solvents were removed in vacuo, and the residue was purified by column chromatography (normal phase, [Biotage SNAP cartridge KP-sil 25 g, 40-63 μm, 60 Å, 50 mL per min, gradient 1% to 10% MeOH in DCM]). The residue was further purified by preparative reversed phase HPLC (Phenomenex Gemini-NX 5 μm C18 110A Axia column, 100×30 mm, eluting with 35 to 45% MeCN/Solvent B over 12.5 min at 30 mL/min [where solvent B is 0.2% of (28% $NH_3/H_2O$) in $H_2O$] and collecting fractions by monitoring at 218 nm) to give ethyl 6-[4-(1H-pyrazol-1-yl)piperidin-1-yl]-2-azaspiro[3.3]heptane-2-carboxylate, Example 1-3 (55.2 mg, 19%) as a colourless oil.

The data for Example 1-3 are in Table 3

Route c

Typical Procedure for the Preparation of Piperidines Via Sodium Triacetoxyborohydride Reductive Amination, Boc-Deprotection and Amide/Carbamate/Urea Formation as Exemplified by the Preparation of Example 2-4, Ethyl 6-{4-[(2S)-1-(methylcarbamoyl)pyrrolidin-2-yl]piperidin-1-yl}-2-azaspiro[3.4]octane-2-carboxylate

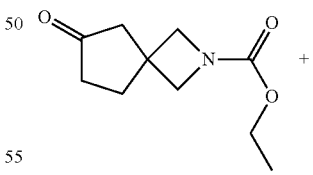

Intermediate 10

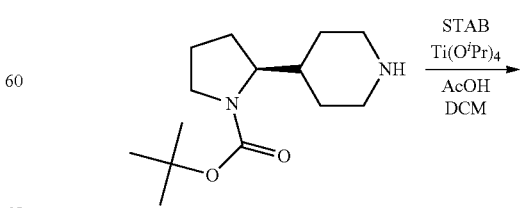

Intermediate 7

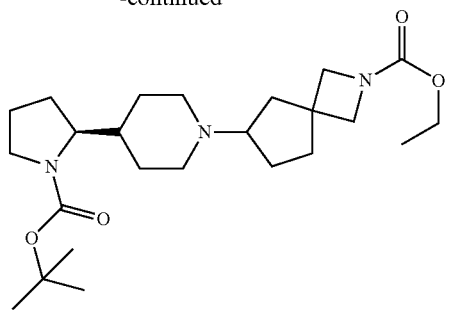

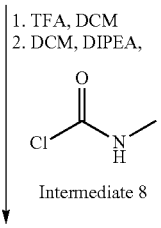

Intermediate 8

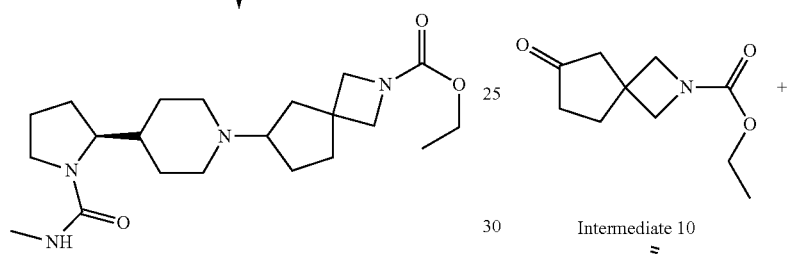

Example 2-4

Ethyl 6-oxo-2-azaspiro[3.4]octane-2-carboxylate (0.15 g, 0.6 mmol) was dissolved in DMF (2 mL) and (S)-tert-Butyl 2-(piperidin-4-yl)pyrrolidine-1-carboxylate (0.12 g, 0.60 mmol) and acetic acid (0.05 mL, 0.9 mmol) were added. The reaction mixture was stirred at rt for 5 h. STAB (0.25 g, 1.2 mmol) was then added and the reaction mixture was stirred overnight under nitrogen at rt. The solvents were removed in vacuo and the crude mixture was redissolved into dichloromethane (25 mL) and extracted with 1.0M NaOH$_{(aq)}$ (3×25 mL). The organic layers were collected, washed with brine (25 mL), passed through a Biotage Phase Separator, and then the residue was concentrated in vacuo to give an inseparable mixture of isomers of ethyl 6-{4-[(2S)-1-(tert-butoxycarbonyl)pyrrolidin-2-yl]piperidin-1-yl}-2-azaspiro[3.4]octane-2-carboxylate (0.26 mg, 99%) as a brown oil.

LCMS (Method D): m/z 436 (M+H)$^+$ (ES$^+$), at 2.30 min, UV inactive.

Ethyl 6-{4-[(2S)-1-(tert-butoxycarbonyl)pyrrolidin-2-yl]piperidin-1-yl}-2-azaspiro[3.4]octane-2-carboxylate (0.26 g, 0.6 mmol) was dissolved in DCM (1.0 mL) and TFA (1.0 mL). The reaction mixture was stirred at rt for 2 h. The volatiles were then removed in vacuo and the residue dissolved DCM (1.0 mL) and Diisopropylethylamine (0.23 mL, 1.37 mmol). Methylaminoformyl chloride (0.23 g, 0.60 mmol) was added and the solution stirred at rt for 2 h. The mixture was poured into dichloromethane (25 mL) and extracted with 1.0M NaOH$_{(aq)}$ (3×25 mL). The organic layers were collected, washed with brine (25 mL), passed through a Biotage Phase Separator, and then the residue was concentrated in vacuo and the residue was purified by column chromatography (normal phase, [Biotage SNAP cartridge KP-sil 25 g, 40-63 μm, 60 Å, 50 mL per min, gradient 1% to 20% 3.5N NH$_3$ in MeOH:DCM) to give ethyl ethyl 6-{4-[(2S)-1-(methylcarbamoyl)pyrrolidin-2-yl]piperidin-1-yl}-2-azaspiro[3.4]octane-2-carboxylate, Example 2-4 (0.11 g, 45%) as a yellow oil.

The data for Example 2-4 are in Table 3

Route d

Typical Procedure for the Preparation of Piperidines Via Sodium Cyanoborohydride Reductive Amination, as Exemplified by the Preparation of Example 2-5, 6-(4-((S)-2-methyl-5-oxopyrrolidin-1-yl)piperidin-1-yl)-2-azaspiro[3.4]octane-2-carboxylate

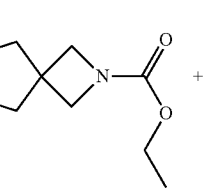

Intermediate 10

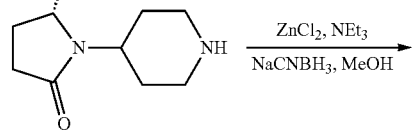

Intermediate 11

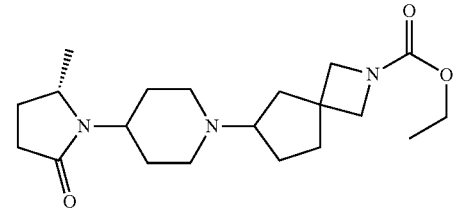

Example 2-5

(S)-5-methyl-1-(piperidin-4-yl)pyrrolidin-2-one (42.0 mg, 0.22 mmol), ethyl 6-oxo-2-azaspiro[3.4]octane-2-carboxylate (45.0 mg, 0.22 mmol), triethylamine (0.06 mL, 0.44 mmol) and ZnCl$_2$ (1.5 mg, 0.01 mmol) were dissolved in MeOH (10 mL) and the reaction mixture stirred at 60° C. for 8 h. The mixture was cooled to 0° C. and NaCNBH$_3$ (19.0 mg, 0.29 mmol) added portionwise. The resulting reaction mixture was stirred at 25° C. for 17 h before the solvents were removed in vacuo and the residue partitioned between H$_2$O (100 mL) and EtOAc (80 mL). The aqueous layer was extracted with EtOAc (2×80 mL) and combined organics dried (Na$_2$SO$_4$) and the solvent removed in vacuo. The crude residue was purified by preparative HPLC [reverse phase (X-BRIDGE C-18, 150×19 mm, 5 μm, 15 mL per min, gradient 25% to 100% (over 20.0 min), 100% (over 3.0 min), then 30% (over 2.0 min), 0.1% NH$_3$ in MeCN/water] to give ethyl 6-(4-((S)-2-methyl-5-oxopyrrolidin-1- yl)piperidin-1-yl)-2-azaspiro[3.4]octane-2-carboxylate, Example 2-5 (10.0 mg, 11%) as a light yellow semi solid.

The data for Example 2-5 are in Table 3

Route e

Typical Procedure for the Preparation of Piperidines Via Sodium Triacetoxyborohydride Reductive Amination, as Exemplified by the Preparation of Example 1-5, racemic ethyl 6-{4-[2-(1,2-oxazol-3-yl)pyrrolidin-1-yl]piperidin-1-yl}-2-azaspiro[3.3]heptane-2-carboxylate

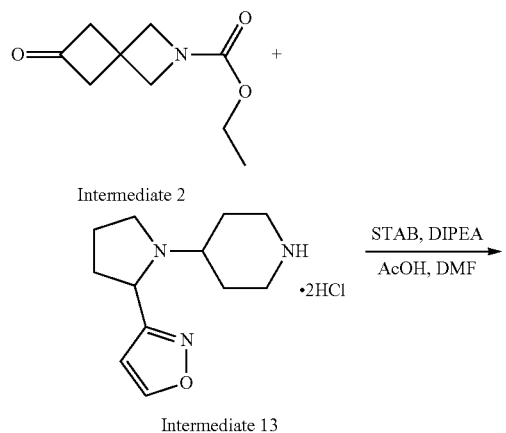

Intermediate 2

Intermediate 13

STAB, DIPEA
AcOH, DMF

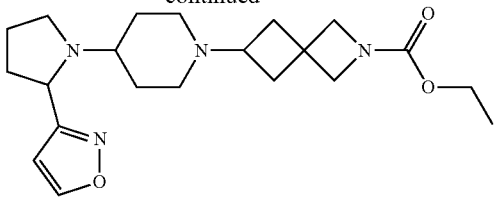

Example 1-5

To a solution of 4-[2-(1,2-oxazol-3-yl)pyrrolidin-1-yl]piperidine dihydrochloride (229 mg, 0.89 mmol) and ethyl 6-oxo-2-azaspiro[3.3]heptane-2-carboxylate (163 mg, 0.89 mmol) in DMF (4 mL) was added DIPEA (0.23 mL, 1.34 mmol) and the mixture stirred at 50° C. under $N_2$ for 2 h. The solution was cooled to rt before addition of STAB (472 mg, 2.23 mmol) and AcOH (0.05 mL, 0.89 mmol) and further heating at 40° C. under $N_2$ for 16 h. The reaction mixture was cooled to rt, quenched with sat. aq. $NaHCO_3$ (10 mL) and concentrated in vacuo. The aqueous layer was extracted with DCM (3×10 mL), combined organics dried (Biotage phase separator cartridge) and the solvent removed in vacuo. The crude residue was purified by column chromatography (normal phase, [Biotage SNAP cartridge KP-sil 25 g, gradient 0 to 10% MeOH in DCM) to yield Example 1-5, racemic ethyl 6-{4-[2-(1,2-oxazol-3-yl)pyrrolidin-1-yl]piperidin-1-yl}-2-azaspiro[3.3]heptane-2-carboxylate (55 mg, 16%) as a yellow gum.

The data for Example 1-5 are in Table 3

TABLE 2

Characterising data and commercial sources for intermediates
Table 2

| Intermediate | Route | Name | Data |
|---|---|---|---|
| 1 | | tert-butyl 6-oxo-2-azaspiro[3.3]heptane-2-carboxylate | Commercially available, CAS: 1181816-12-5 |
| 2 | Route 1 and Intermediates 1 and 3 | ethyl 6-oxo-2-azaspiro[3.3]heptane-2-carboxylate | NMR $^1$H NMR (400 MHz, $CDCl_3$) δ: 1.26 (t, J = 6.6 Hz, 3H), 3.31 (s, 4H), 4.06-4.24 (m, 6H) |
| 3 | | ethyl chloroformate | Commercially available, CAS: 541-41-3 |
| 4 | | methyl chloroformate | Commercially available, CAS: 79-22-1 |
| 5 | | 4-(1-Methyl-1H-imidazol-2-yl-piperidine hydrochloride | Commercially available, CAS: 1198420-89-1 |
| 6 | | 4-(1H-pyrazol-1-yl)piperidine | Commercially available, CAS: 762240-09-5 |
| 7 | | (S)-tert-butyl 2-(piperidin-4-yl)pyrrolidine-1-carboxylate | Commercially available, CAS: 1449131-15-0 |
| 8 | | methylaminoformyl chloride | Commercially available, CAS: 6452-47-7 |
| 9 | | tert-butyl 6-oxo-2-azaspiro[3.4]octane-2-carboxylate | Commercially available, CAS: 1363382-39-1 |
| 10 | Route 1 and Intermediates 3 and 9 | Ethyl 6-oxo-2-azaspiro[3.4]octane-2-carboxylate | NMR $^1$H NMR (400 MHz, MeOD-$d_4$) δ: 1.24 (q, J = 7.0 Hz, 3H), 2.16-2.32 (m, 4H), 2.47 (s, 2H), 3.85-3.97 (m, 4H), 4.08 (q, J = 7.0 Hz, 2H) |
| 11 | Route 3 and intermediate 18 and 26 | (5S)-5-methyl-1-(piperidin-4-yl)pyrrolidin-2-one | LCMS (Method E) m/z 183 (M + H)$^+$ (ES+) at 2.57 min, UV inactive |
| 12 | | (5R)-5-(hydroxymethyl)pyrrolidin-2-one | Commercially available, CAS: 66673-40-3 |
| 13 | Route 8 and intermediate 14 | 4-[2-(1,2-oxazol-3-yl)pyrrolidin-1-yl]piperidine dihydrochloride | LCMS (Method C) m/z 222 (M + H)$^+$ (ES+) at 0.79 min, UV active |
| 14 | Route e and intermediates 15 and 16 | tert-butyl 4-[2-(1,2-oxazol-3-yl)pyrrolidin-1-yl]piperidine-1-carboxylate | LCMS (Method D) m/z 322 (M + H)$^+$ (ES+) at 2.14 min, UV active |

TABLE 2-continued

Characterising data and commercial sources for intermediates
Table 2

| Intermediate | Route | Name | Data |
|---|---|---|---|
| 15 | | tert-butyl 4-oxopiperidine-1-carboxylate | Commercially available, CAS: 79099-07-3 |
| 16 | | 3-(pyrrolidin-2-yl)-1,2-oxazole hydrochloride | Commercially available, CAS: 1332528-62-7 |
| 17 | Route 1 and Intermediates 4 and 9 | methyl 6-oxo-2-azaspiro[3.4]octane-2-carboxylate | (LC/MS Method I): m/z 184 (M + H)+ (ES+), at 2.47 min, UV active. |
| 18 | Route 2 and intermediate 12 | (S)-5-methylpyrrolidin-2-one | LCMS (Method F): m/z 100 (M + H) + (ES+), at 0.79 min, UV inactive. |
| 19 | Route 2 and intermediate 20 | (R)-5-methylpyrrolidin-2-one | LCMS (Method F): m/z 100 (M + H) + (ES+), at 0.63 min, UV inactive |
| 20 | | (5S)-5-(hydroxymethyl)pyrrolidin-2-one | Commercially available, CAS: 17342-08-4 |
| 21 | Route 3 and intermediate 19 and 26 | (5R)-5-methyl-1-(piperidin-4-yl)pyrrolidin-2-one | LCMS (Method E) m/z 183 (M + H)+ (ES+) at 2.58 min, UV inactive |
| 22 | Route 4 and intermediate 20 | (R)-5-ethylpyrrolidin-2-one | LCMS (Method E) m/z 114 (M + H)+ (ES+) at 2.33 min, UV inactive |
| 23 | Route 4 and intermediate 12 | (S)-5-ethylpyrrolidin-2-one | LCMS (Method E) m/z 114 (M + H)+ (ES+) at 2.36 min, UV inactive |
| 24 | Route 3 and intermediate 22 and 26 | (5R)-5-ethyl-1-(piperidin-4-yl)pyrrolidin-2-one | LCMS (Method E) m/z 197 (M + H)+ (ES+) at 3.12 min, UV inactive |
| 25 | Route 3 and intermediate 23 and 26 | (5S)-5-ethyl-1-(piperidin-4-yl)pyrrolidin-2-one | LCMS (Method E) m/z 197 (M + H)+ (ES+) at 3.03 min, UV inactive |
| 26 | | 4-iodopyridine | Commercially available, CAS: 15854-87-2 |
| 27 | | (tert-butoxycarbonyl)-D-proline | Commercially available, CAS: 37784-17-1 |
| 28 | | thiazolidinedione | Commercially available, CAS: 2295-31-0 |
| 29 | | tert-butyl 4-oxopiperidine-1-carboxylate | Commercially available, CAS: 79099-07-3 |
| 30 | Route 5 and intermediate 27, 28 and 29 | (R)-3-methyl-5-(1-(piperidin-4-yl)pyrrolidin-2-yl)oxazol-2(3H)-one. TFA | LCMS (Method F): m/z 252 (M + H) + (ES+), at 2.77 min, UV inactive |
| 31 | | (R)-1-tert-Butyl 2-methyl 4-oxopyrrolidine-1,2-dicarboxylate | Commercially available, CAS: 256487-77-1 |
| 32 | Route 6 and intermediate 29 and 31 | 4-[(2R)-4,4-difluoro-2-(hydroxymethyl)pyrrolidin-1-yl]piperidine. TFA | LCMS (Method E) m/z 221 (M + H)+ (ES+) at 2.47 min, UV inactive |
| 33 | Route 7 and intermediate 27, 29 and 34 | tert-butyl 4-[(2R)-2-(1,3-oxazol-5-yl)pyrrolidin-1-yl]piperidine-1-carboxylate | LCMS (Method A) m/z 266 (M + H − 56)+ (ES+) at 2.04 min, UV inactive |
| 34 | | (p-Tolylsulfonyl)methyl isocyanide, (TosMIC) | Commercially available, CAS: 36635-61-7 |

TABLE 3

| Ex. No. | Name | Intermediate | Synthetic method | $^1$H NMR | LCMS Method | LCMS data |
|---|---|---|---|---|---|---|
| 1-1 | Methyl 6-[4-(1-methyl-1H-imidazol-2-yl)piperidin-1-yl]-2-azaspiro[3.3]heptane-2-carboxylate | 1, 4 and 5 | a | (400 MHz, CDCl$_3$) δ: 1.77-2.00 (m, 6 H), 2.01-2.12 (m, 2 H), 2.31 (ddd, J = 9.7, 6.9, 2.9 Hz, 2 H), 2.54-2.67 (m, 2 H), 2.93 (d, J = 10.9 Hz, 2 H), 3.59 (s, 3 H), 3.65 (s, 3 H), 3.88 (s, 2 H), 3.99 (s, 2 H), 6.77 (d, J = 1.2 Hz, 1 H), 6.93 (d, J = 1.2 Hz, 1 H). | B | m/z 319 (M+H)+ (ES+), at 2.80 min, UV active |

TABLE 3-continued

| Ex. No. | Name | Intermediate | Synthetic method | $^1$H NMR | LCMS Method | LCMS data |
|---|---|---|---|---|---|---|
| 1-2 | Ethyl 6-[4-(1-methyl-1 H-imidazol-2-yl)piperidin-1-yl]-2-azaspiro[3.3]heptane-2-carboxylate | 1, 3 and 5 | a | (400 MHz, CDCl$_3$) δ: 1.23 (t, J = 7.1 Hz, 3 H), 1.47-2.05 (m, 5 H), 2.07-2.52 (m, 4 H), 2.53-2.86 (m, 2 H), 2.87-3.17 (m, 2 H), 3.17-3.48 (m, 2 H), 3.60 (s, 3 H), 3.81-4.13 (m, 5 H), 6.75-6.84 (m, 1 H), 6.86-6.96 (m, 1 H). | B | m/z 333 (M+H)+ (ES+), at 3.26 min, UV inactive |
| 1-3 | Ethyl 6-[4-(1H-pyrazol-1-yl)piperidin-1-yl]-2-azaspiro[3.3]heptane-2-carboxylate | 2 and 6 | b | (400 MHz, CDCl$_3$) δ: 1.20 (t, J = 6.6 Hz, 3 H), 1.78-2.19 (m, 8 H), 2.30 (t, J = 7.8 Hz, 2 H), 2.54-2.67 (m, 1 H), 2.92 (d, J = 7.8 Hz, 2 H), 3.85 (s, 2 H), 3.96 (s, 2 H), 4.00-4.21 (m, 3 H), 6.22 (s, 1 H), 7.39 (s, 1 H), 7.46 (s, 1 H) | B | m/z 319 (M+H)+ (ES+), at 2.84 min, UV inactive. |
| 1-4 | Ethyl 6-{4-[(2S)-1-(methylcarbamoyl)pyrrolidin-2-yl]piperidin-1-yl}-2-azaspiro[3.3]heptane-2-carboxylate | 2, 7 and 8 | c | (400 MHz, MeOD-d$_4$) δ: 1.21 (t, J = 7.2 Hz, 3 H), 1.25-1.41 (m, 3 H), 1.51-1.65 (m, 2 H), 1.67-1.97 (m, 8 H), 1.98-2.09 (m, 2 H), 2.29-2.38 (m, 2 H), 2.62 (d, J = 6.6 Hz, 1 H), 2.71 (s, 3 H), 2.86-2.99 (m, 2 H), 3.20-3.28 (m, 2 H), 3.81-3.90 (m, 2 H), 3.94-4.01 (m, 1 H), 4.05 (q, J = 7.2 Hz, 2 H) | B | m/z 379 (M+H)+ (ES+), at 2.68 min, UV inactive |
| 1-5 | Racemic: Ethyl 6-{4-[2-(1,2-oxazol-3-yl)pyrrolidin-1-yl]piperidin-1-yl}-2-azaspiro[3.3]heptane-2-carboxylate | 2 and 13 | e | (400 MHz, DMSO-d$_6$) δ: 1.11 (t, J = 7.0 Hz, 3 H), 1.18-1.39 (m, 2 H), 1.47-2.31 (m, 14 H), 2.56-2.78 (m, 3 H), 2.82-2.93 (m, 1 H), 3.65-4.00 (m, 6 H), 4.10-4.18 (m, H), 6.24-6.29 (m, 1 H), 8.39 (s, 1 H) | G | m/z 389 (M+H)+ (ES+), at 3.32 min, UV active |
| 1-6 | Ethyl 6-{4-[(2R)-2-(1,3-oxazol-5-yl)pyrrolidin-1-yl[piperidin-1-yl}-2-azaspiro[3.3]heptane-2-carboxylate | 1, 3 and 33 | 8 followed by a | (400 MHz, DMSO-d$_6$) δ: 1.11 (t, J = 7.0 Hz, 3 H), 1.19-1.40 (m, 3 H), 1.52-1.61 (m, 3 H), 1.67-2.04 (m, 8 H), 2.15-2.24 (m, 3 H), 2.39-2.47 (m, 1 H), 2.56-2.70 (m, 3 H), 2.78-2.85 (m, 1 H), 3.66-3.89 (m, 4 H), 3.94 (q, J = 7.0 Hz, 2 H), 4.01-4.06 (m, 1 H), 6.92 (s, 1 H), 8.19 (s, 1 H) | E | m/z 389 (M+H)+ (ES+), at 3.54 min, UV active |
| 1-7 | Ethyl 6-{4-[(2R)-2-(3-methyl-2-oxo-2,3-dihydro-1,3-oxazol-5yl)pyrrolidin-1-yl]piperidin-1-yl }-2-azaspiro[3.3]heptane-2-carboxylate | 2 and 30 | d | (400 MHz, MeOD-d$_4$) δ: 1.23 (t, J = 7.0 Hz, 3 H), 1.45-1.65 (m, 2 H), 1.75-2.12 (m, 10 H), 2.30-2.51 (m, 3 H), 2.56-2.78 (m, 2 H), 2.82-2.98 (m, 3 H), 3.19 (s, 3 H), 3.80-4.03 (m, 5 H), 4.07 (q, J = 7.0 Hz, 2 H), 6.71 (s, 1 H) | I | m/z 419 (M+H)+ (ES+), at 3.50 min, UV active |
| 1-8 | Ethyl 6-{4-[(2S)-2-methyl-5-oxopyrrolidin-1-yl]piperidin-1-yl}-2-azaspiro[3.3]heptane-2-carboxylate | 2 and 11 | d | (400 MHz, MeOD-d$_4$) δ:1.24 (t, J = 7.0 Hz, 3 H), 1.31 (d, J = 6.0 Hz, 3 H), 1.62-1.75 (m, 2 H), 1.77-2.00 (m, 4 H), 2.02-2.42 (m, 7 H), 2.43-2.56 (m, 1 H), 2.60-2.74 (m, 1 H), 2.90-3.05 (m, 2 H), 3.60-3.72 (m, 1 H), 3.82-4.02 (m, 5 H), 4.08 (q, J = 7.0 Hz, 2 H) | I | m/z 350 (M+H)+ (ES+), at 3.43 min, UV active |
| 1-9 | Ethyl 6-14-[(2R)-2-methyl-5-oxopyrrolidin-1-yl]piperidin-1-yl}-2-azaspiro[3.3]heptane-2-carboxylate | 2 and 21 | d | (400 MHz, MeOD-d$_4$) δ:1.24 (t, J = 7.0 Hz, 3 H), 1.31 (d, J = 6.5 Hz, 3 H), 1.62-1.74 (m, 2 H), 1.77-1.99 (m, 4 H), 2.01-2.43 (m, 7 H), 2.44-2.56 (m, 1 H), 2.63-2.74 (m, 1 H), 2.92-3.05 (m, 2 H), 3.62-3.73 (m, 1 H), 3.83-4.03 (m, 5 H), 4.08 (q, J = 7.0 Hz, 2 H) | I | m/z 350 (M+H)+ (ES+), at 3.40 min, UV active |
| 1-10 | Ethyl 6-{4-[(2S)-2-ethyl-5-oxopyrrolidin-1-yl]piperidin-1-yl}-2-azaspiro[3.3]heptane-2-carboxylate | 2 and 25 | d | (400 MHz, MeOD-d$_4$) δ: 0.93 (t, J = 7.5 Hz, 3 H), 1.24 (t, J = 7.0 Hz, 3 H), 1.49-1.61 (m, 1 H), 1.65-1.73 (m, 1 H), 1.77-2.52 (m, 14 H), 2.62-2.74 (m, 1 H), 2.90-3.05 (m, 2 H), 3.55-3.67 (m, 1 H), 3.70-3.78 (m, 1 H), 3.85-4.03 (m, 4 H), 4.08 (q, J = 7.0 Hz, 2 H) | I | m/z 364 (M+H)+ (ES+), at 3.67 min, UV active |
| 1-11 | Ethyl 6-{4-[(2R)-2-ethyl-5-oxopyrrolidin-1-yl]piperidin-1-yl}-2-azaspiro[3.3]heptane-2-carboxylate | 2 and 24 | d | (400 MHz, MeOD-d$_4$) δ: 0.94 (t, J = 7.5 Hz, 3 H), 1.24 (t, J = 7.0 Hz, 3 H), 1.49-1.62 (m, 1 H), 1.66-1.73 (m, 1 H), 1.78-2.53 (m, 14 H), 2.62-2.73 (m, 1 H), 2.89-3.04 (m, 2 H), 3.56-3.66 (m, 1 H), 3.70-3.78 (m, 1 H), 3.87-4.03 (m, 4 H), 4.08 (q, J = 7.0 Hz, 2 H) | I | m/z 364 (M+H)+ (ES+), at 3.71 min, UV active |
| 1-12 | Ethyl 6-{4-[(2R)-4,4-difluoro-2-(hydroxymethyl)pyrrolidin-1-yl]piperidin-1-yl}-2-azaspiro[3.3]heptane-2-carboxylate | 2 and 32 | d | (400 MHz, MeOD-d$_4$) δ: 1.24 (t, J = 7.0 Hz, 3 H), 1.42-1.60 (m, 2 H), 1.78-1.92 (m, 4H), 2.02-2.43 (m, 7 H), 2.60-2.80 (m, 2 H), 2.87-3.28 (m, 5 H), 3.48-3.64 (m, 2 H), 3.85-4.02 (m, 4 H), 4.08 (q, J = 7.0 Hz, 2 H) | I | m/z 388 (M+H)+ (ES+), at 3.49 min, UV active |

TABLE 3-continued

| Ex. No. | Name | Intermediate | Synthetic method | $^1$H NMR | LCMS Method | LCMS data |
|---|---|---|---|---|---|---|
| 2-1 | Racemic: Methyl 6-[4-(1-methyl-1H-imidazol-2-yl)piperidin-1-yl]-2-azaspiro[3.4]octane-2-carboxylate | 4, 5 and 9 | a | (400 MHz, CDCl$_3$) δ: 1.50-2.16 (m, 12 H), 2.52-2.68 (m, 2 H), 3.02-3.11 (m, 2 H), 3.59 (s, 3 H), 3.66 (s, 3 H), 3.74-3.92 (m, 4 H), 6.77 (d, J = 1.2 Hz, 1 H), 6.93 (d, J = 1.2 Hz, 1 H) | A | m/z 333 (M+H)+ (ES+), at 2.95 min, UV active |
| 2-2 | Racemic: Ethyl 6-[4-(1-methyl-1H-imidazol-2-yl)piperidin-1-yl]-2-azaspiro[3.4]octane-2-carboxylate | 10, 3 and 5 | a | (400 MHz, CDCl$_3$) δ: 1.24 (t, J = 7.3 Hz, 3 H), 1.51-2.41 (m, 12 H), 2.43-3.41 (m, 4 H), 3.61 (s, 3 H), 3.78 (s, 2 H), 3.82-4.03 (m, 2 H), 4.10 (d, J = 7.3 Hz, 2 H), 6.80 (s, 1 H), 6.93 (s, 1 H) | A | m/z 347 (M+H)+ (ES+), at 3.41 min, UV inactive |
| 2-3 | Racemic: Ethyl 6-[4-(1H-pyrazol-1-yl)piperidin-1-yl]-2-azaspiro[3.4]octane-2-carboxylate | 10, 3 and 6 | b | (400 MHz, CDCl$_3$) δ: 1.22 (t, J = 6.6 Hz, 3 H), 1.48-1.63 (m, 1 H), 1.65-2.25 (m, 11 H), 2.51-2.68 (m, 1 H), 3.00-3.19 (m, 2 H), 3.67-3.94 (m, 4 H), 4.00-4.23 (m, 3 H), 6.24 (s, 1 H), 7.42 (s, 1 H), 7.48 (s, 1 H) | A | m/z 333 (M+H)+ (ES+), at 3.06 min, UV inactive |
| 2-4 | Racemic: Ethyl 6-{4-[(2S)-1-(methylcarbamoyl)pyrrolidin-2-yl]piperidin-1-yl}-2-azaspiro[3.4]octane-2-carboxylate | 10, 7 and 8 | c | (400 MHz, MeOD-d$_4$) δ:1.22 (t, J = 7.2 Hz, 3 H), 1.26-1.45 (m, 2 H), 1.46-2.00 (m, 15 H), 2.15 (dd, J = 11.7, 7.8 Hz, 1 H), 2.52-2.63 (m, 1 H), 2.70 (s, 3 H), 3.00-3.11 (m, 2 H), 3.21-3.28 (m, 1 H), 3.70-3.91 (m, 5 H), 4.06 (q, J = 7.2 Hz, 2 H), NH not observed | A | m/z 393 (M+H)+ (ES+), at 2.89 min, UV inactive |
| 2-5 | Racemic: ethyl 6-{4-[(2S)-2-methyl-5-oxopyrrolidin-1-yl]piperidin-1-yl}-2-azaspiro[3.4]octane-2-carboxylate | 10 and 11 | d | (400 MHz, MeOD-d$_4$) δ:1.24 (t, J = 7.0 Hz, 3 H), 1.31 (d, J = 6.0 Hz, 3 H), 1.45-2.71 (m, 17 H), 3.07-3.18 (m, 2 H), 3.63-3.98 (m, 6 H), 4.09 (q, J = 7.0 Hz, 2 H) | F | m/z 364 (M+H)+ (ES+), at 3.52 min, UV active |
| 2-6 | Racemic: Ethyl 6-{4-[(2S)-2-ethyl-5-oxopyrrolidin-1-yl]piperidin-1-yl}-2-azaspiro[3.4]octane-2-carboxylate | 10 and 25 | d | (400 MHz, MeOD-d$_4$) δ: 0.94 (t, J = 7.5 Hz, 3 H), 1.24 (t, J = 7.0 Hz, 3 H), 1.47-1.62 (m, 2 H), 1.65-2.36 (m, 15 H), 2.42-2.52 (m, 1 H), 2.61-2.72 (m, 1 H), 3.05-3.18 (m, 2 H), 3.57-3.70 (m, 1 H), 3.72-3.97 (m, 5 H), 4.08 (q, J = 7.0 Hz, 2 H) | I | m/z 378 (M+H)+ (ES+), at 3.87 min, UV active |
| 2-7 | Racemic: Ethyl 6-{4-[(2R)-2-methyl-5-oxopyrrolidin-1-yl]piperidin-1-yl}-2-azaspiro[3.4]octane-2-carboxylate | 10 and 21 | d | (400 MHz, MeOD-d$_4$) δ:1.24 (t, J = 7.0 Hz, 3 H), 1.32 (d, J = 6.5 Hz, 3 H), 1.48-2.32 (m, 15 H), 2.42-2.56 (m, 1 H), 2.61-2.71 (m, 1 H), 3.05-3.17 (m, 2 H), 3.61-3.73 (m, 1 H), 3.74-3.98 (m, 5 H), 4.08 (q, J = 7.0 Hz, 2 H) | I | m/z 364 (M+H)+ (ES+), at 3.56 min, UV active |
| 2-8 | Isomer 1: Methyl 6-{4-[(2R)-2-ethyl-5-oxopyrrolidin-1-yl]piperidin-1-yl}-2-azaspiro[3.4]octane-2-carboxylate | 17 and 24 | d | (400 MHz, MeOD-d$_4$) δ: 0.93 (t, J = 7.0 Hz, 3 H), 1.44-1.60 (m, 2 H), 1.63-2.35 (m, 15 H), 2.40-2.51 (m, 1 H), 2.56-2.68 (m, 1 H), 3.03-3.15 (m, 2 H), 3.55-3.63 (m, 1 H), 3.64 (s, 3 H), 3.67-3.95 (m, 5 H) | I | m/z 364 (M+H)+ (ES+), at 3.64 min, UV active |
| 2-8 | Isomer 2: Methyl 6-{4-[(2R)-2-ethyl-5-oxopyrrolidin-1-yl]piperidin-1-yl}-2-azaspiro[3.4]octane-2-carboxylate | 17 and 24 | d | (400 MHz, MeOD-d$_4$) δ: 0.93 (t, J = 7.0 Hz, 3 H), 1.44-1.61 (m, 2 H), 1.63-2.33 (m, 15 H), 2.38-2.51 (m, 1 H), 2.57-2.69 (m, 1 H), 3.02-3.16 (m, 2 H), 3.55-3.63 (m, 1 H), 3.64 (s, 3 H), 3.67-3.95 (m, 5 H) | I | m/z 364 (M+H)+ (ES+), at 3.64 min, UV active |
| 2-9 | Racemic: Ethyl 6-{4-[(2R)-2-ethyl-5-oxopyrrolidin-1-yl]piperidin-1-yl}-2-azaspiro[3.4]octane-2-carboxylate | 10 and 24 | d | (400 MHz, MeOD-d$_4$) δ: 0.94 (t, J = 7.5 Hz, 3 H), 1.24 (t, J = 7.0 Hz, 3 H), 1.48-1.62 (m, 2 H), 1.65-2.33 (m, 15 H), 2.43-2.51 (m, 1 H), 2.62-2.72 (m, 1 H), 3.06-3.18 (m, 2 H), 3.58-3.70 (m, 1 H), 3.72-3.97 (m, 5 H), 4.08 (q, J = 7.0 Hz, 2 H) | I | m/z 378 (M+H)+ (ES+), at 3.83 min, UV active |
| 2-10 | Racemic: Ethyl 6-{4-[(2R)-4,4-difluoro-2-(hydroxymethyl)pyrrolidin-1-yl]piperidin-1-yl}-2-azaspiro[3.4]octane-2-carboxylate | 10 and 32 | d | (400 MHz, MeOD-d$_4$) δ: 1.24 (t, J = 7.0 Hz, 3 H), 1.42-1.63 (m, 3 H), 1.67-1.77 (m, 1 H), 1.80-2.10 (m, 7 H), 2.12-2.28 (m, 2 H), 2.29-2.43 (m, 1 H), 2.57-2.80 (m, 2 H), 3.03-3.28 (m, 5 H), 3.48-3.65 (m, 2 H), 3.75-3.96 (m, 4 H), 4.09 (q, J = 7.0 Hz, 2 H) | I | m/z 402 (M+H)+ (ES+), at 3.64 min, UV active |
| 2-11 | Isomer 1: Methyl 6-{4-[(2R)-2-(1,3-oxazol-5-yl)pyrrolidin-1-yl]piperidin-1-yl}-2-azaspiro[3.4]octane-2-carboxylate | 4, 9 and 33 | 8 followed by a | (400 MHz, MeOD-d$_4$) δ: 1.43-2.06 (m, 14 H), 2.10-2.23 (m, 2 H), 2.29-2.43 (m, 1 H), 2.53-2.65 (m, 1 H), 2.73-2.85 (m, 1 H), 2.92-3.10 (m, 3 H), 3.65 (s, 3 H), 3.73-3.99 (m, 4 H), 4.15-4.25 (m, 1 H), 7.02 (s, 1 H), 8.16 (s, 1 H) | I | m/z 389 (M+H)+ (ES+), at 3.44 min, UV active |
| 2-11 | Isomer 2: Methyl 6-{4-[(2R)-2-(1,3-oxazol-5-yl)pyrrolidin-1-yl]piperidin-1-yl}-2-azaspiro[3.4]octane-2-carboxylate | 4, 9 and 33 | 8 followed by a | (400 MHz, MeOD-d$_4$) δ: 1.45-2.05 (m, 14 H), 2.08-2.24 (m, 2 H), 2.28-2.43 (m, 1 H), 2.53-2.63 (m, 1 H), 2.73-2.84 (m, 1 H), 2.93-3.10 (m, 3 H), 3.65 (s, 3 H), 3.73-3.98 (m, 4 H), 4.15-4.25 (m, 1 H), 7.02 (s, 1 H), 8.16 (s, 1 H) | I | m/z 389 (M+H)+ (ES+), at 3.44 min, UV active |

TABLE 3-continued

| Ex. No. | Name | Intermediate | Synthetic method | $^1$H NMR | LCMS Method | LCMS data |
|---|---|---|---|---|---|---|
| 2-12 | Racemic: Ethyl 6-{4-[(2R)-2-(1,3-oxazol-5-yl)pyrrolidin-1-yl]piperidin-1-yl}-2-azaspiro[3.4]octane-2-carboxylate | 3, 9 and 33 | 8 followed by a | (400 MHz, MeOD-d$_4$) δ: 1.21 (t, J = 7.0 Hz, 3 H), 1.46-2.27 (m 16 H), 2.30-2.43 (m, 1 H), 2.57-2.80 (m, 2 H), 2.90-3.10 (m, 3 H), 3.70-3.93 (m, 4 H), 4.06 (q, J = 7.0 Hz, 2 H), 4.13-4.20 (m, 1 H), 7.00 (s, 1 H), 8.12 (s, 1 H) | E | m/z 403 (M+H)+ (ES+), at 3.74 min, UV active |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader. pEC$_{50}$ and E$_{max}$ figures were calculated from the resulting data for each receptor subtype.

The results are set out in Table 4 below.

TABLE 4

| | Muscarinic Activity | | | |
|---|---|---|---|---|
| Ex.No. | pEC$_{50}$ M$_1$ (% Emax cf. ACh) | pEC$_{50}$ M$_2$ (% Emax cf. ACh) | pEC$_{50}$ M$_3$ (% Emax cf. ACh) | pEC$_{50}$ M$_4$ (% Emax cf. ACh) |
| ACh | 8.3 (102) | 7.8 (105) | 8.1 (115) | 8.1 (110) |
| Example 1-1 | 5.5 (113) | NT | NT | 6.5 (73) |
| Example 1-2 | 5.0 (100) | NT | NT | 5.9 (100) |
| Example 1-4 | 6.1 (71) | <4.7 (6) | <4.7 (7) | 7.8 (97) |
| Example 1-5 (racemic) | <4.7 (18) | <4.7 (67) | <4.7 (10) | 7.4 (64) |
| Example 1-6 | 6.2 (67) | <4.7 (4) | <4.7 (16) | 7.9 (105) |
| Example 1-7 | <4.7 (12) | <4.7 (10) | <4.7 (6) | 7.4 (49) |
| Example 1-8 | 6.1 (67) | NT | NT | 6.7 (78) |
| Example 1-9 | 5.8 (101) | NT | NT | 6.8 (117) |
| Example 1-12 | 6.6 (63) | <4.7 (7) | <4.7 (11) | 7.5 (88) |
| Example 2-1 (racemic) | 6.9 (42) | <4.7 (17) | <4.7 (9) | 7.8 (82) |
| Example 2-2 (racemic) | 6.3 (7) | <4.7 (7) | <4.7 (5) | 7.5 (102) |
| Example 2-3 (racemic) | 8.4 (105) | <4.7 (2) | <4.7 (5) | 9.0 (94) |
| Example 2-4 (racemic) | <4.7 (39) | <4.7 (4) | <4.7 (2) | 8.5 (56) |
| Example 2-5 (racemic) | 6.8 (38) | <4.7 (6) | <4.7 (3) | 7.9 (36) |
| Example 2-6 (racemic) | 7.8 (71) | <4.7 (8) | <4.7 (13) | 8.1 (59) |
| Example 2-7 (racemic) | 7.4 (71) | <4.7 (9) | <4.7 (53) | 8.4 (69) |
| Example 2-9 (racemic) | 7.4 (100) | <4.7 (11) | <4.7 (8) | 8.5 (123) |
| Example 2-10 (racemic) | <4.7 (6) | NT | NT | 8.2 (32) |
| Example 2-11 (Isomer 2) | <4.7 (24) | <4.7 (6) | <4.7 (4) | 7.1 (100) |
| Example 2-12 (Isomer 2) | 7.5(50) | <4.7 (7) | <4.7 (5) | 9.0 (114) |

NT—Not tested

Example B

Pharmaceutical Formulations (i) Tablet Formulation

A tablet composition containing a compound of the formula (1) or formula (1a) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) or formula (1a) with 100 mg lactose and optionally 1% by weight of magnesium stearate and filling the resulting mixture into standard opaque hard gelatin capsules.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1a):

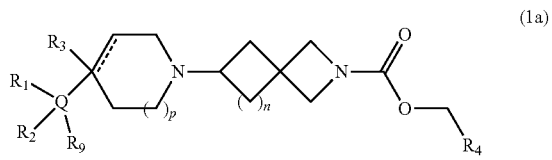

(1a)

or a salt thereof, wherein n is 1;

p is 1;

Q is a five, six or seven membered monocyclic heterocyclic ring containing 1, 2, 3 or 4 heteroatom ring members selected from N, O and S;

$R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$; $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

$R^2$ is selected from hydrogen; fluorine; chlorine; bromine; cyano; hydroxy; methoxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$; $SO_2R^5$; and a $C_{1-6}$ non-aromatic hydrocarbon group; or $R^1$ and $R^2$ can be joined together to form a 6-membered fused aromatic ring;

$R^9$ is selected from hydrogen; $CH_3$; $CH_2OH$; $CH(CH_3)OH$; $C(CH_3)_2OH$; and $COOCH_3$;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^5$, $R^6$ and $R^7$ are the same or different and each is independently selected from hydrogen; a non-aromatic $C_{1-4}$ hydrocarbon group optionally substituted with one or more fluorine atoms; and a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine; chlorine, bromine, cyano, hydroxy, methoxy, amino, and a cycloalkyl; heterocycloalkyl; aryl; or heteroaryl group;

and the dotted line indicates an optional second carbon-carbon bond, provided that when a second carbon-carbon bond is present, then $R^3$ is absent.

2. The compound according to claim 1 of the formula (1):

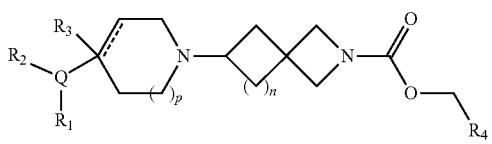

(1)

or a salt thereof, wherein
n is 1;
p is 1;
Q is a five, six or seven membered monocyclic heterocyclic ring containing 1, 2, 3 or 4 heteroatom ring members selected from N, O and S;

$R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$; $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

$R^2$ is selected from hydrogen; fluorine; chlorine; bromine; cyano; hydroxy; methoxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$; $SO_2R^5$; and a $C_{1-6}$ non-aromatic hydrocarbon group; or $R^1$ and $R^2$ can be joined together to form a 6-membered fused aromatic ring;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^5$, $R^6$ and $R^7$ are the same or different and each is independently selected from hydrogen; a non-aromatic $C_{1-4}$ hydrocarbon group optionally substituted with one or more fluorine atoms; and a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine, chlorine, bromine, cyano, hydroxy, methoxy, amino, and a cycloalkyl; heterocycloalkyl; aryl; or heteroaryl group;

and the dotted line indicates an optional second carbon-carbon bond, provided that when a second carbon-carbon bond is present, then $R^3$ is absent.

3. The compound according to claim 1, or a salt thereof, wherein the heterocyclic ring as Q is aromatic.

4. The compound according to claim 3, or a salt thereof, wherein the heterocyclic ring as Q is aromatic and contains one or two nitrogen atoms.

5. The compound according to claim 4, or a salt thereof, wherein Q is (i) an imidazole ring or (ii) a pyrazole ring.

6. The compound according to claim 1, or a salt thereof, wherein $R^1$ is selected from hydrogen; fluorine; cyano; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $SO_2R^5$; and a $C_{1-4}$ non-aromatic hydrocarbon group which is optionally substituted with one to six fluorine atoms.

7. The compound according to claim 6, or a salt thereof, wherein $R^1$ is selected from hydrogen; $NH_2$; $COR^5$; $COOR^5$; and a $C_{1-4}$ saturated non-aromatic hydrocarbon group which is optionally substituted with one to six fluorine atoms, and wherein $R^5$ is selected from $C_{1-4}$ alkyl.

8. The compound according to claim 6, or a salt thereof, wherein $R^1$ is selected from hydrogen; methyl; ethyl;

COOMe; COOEt; COMe; COEt; CONH$_2$; CF$_3$; CONHMe; CON(Me)$_2$; COCF$_3$; CO-cyclopropyl; CO-cyclobutyl; CONHEt; COH; NH$_2$; and OMe.

9. The compound according to claim 1, or a salt thereof, wherein R$^2$ is hydrogen.

10. The compound according to claim 1, or a salt thereof, wherein R$^3$ is present and the optional second carbon-carbon bond is absent.

11. The compound according to claim 1, or a salt thereof, wherein R$^3$ is selected from hydrogen; fluorine; hydroxy; methoxy; and cyano.

12. The compound according to claim 11, or a salt thereof, wherein R$^3$ is hydrogen.

13. The compound according to claim 1, or a salt thereof, wherein R$^9$ is hydrogen or CH$_2$OH.

14. The compound according to claim 1, or a salt thereof, wherein R$^4$ is selected from hydrogen and methyl.

15. The compound according to claim 1, or a salt thereof, having muscarinic M$_1$ receptor and/or M$_4$ receptor agonist activity.

16. A pharmaceutical composition comprising a compound according to claim 1, or a salt thereof, and a pharmaceutically acceptable excipient.

17. The compound according to claim 1 which is selected from the group consisting of:
   Methyl 6-[4-(1-methyl-1H-imidazol-2-yl)piperidin-1-yl]-2-azaspiro[3.3]heptane-2-carboxylate;
   Ethyl 6-[4-(1-methyl-1H-imidazol-2-yl)piperidin-1-yl]-2-azaspiro[3.3]heptane-2-carboxylate;
   Ethyl 6-[4-(1H-pyrazol-1-yl)piperidin-1-yl]-2-azaspiro[3.3]heptane-2-carboxylate;
   Ethyl 6-{4-[(2S)-1-(methylcarbamoyl)pyrrolidin-2-yl]piperidin-1-yl}-2-azaspiro[3.3]heptane-2-carboxylate;
   Ethyl 6-{4-[2-(1,2-oxazol-3-yl)pyrrolidin-1-yl]piperidin-1-yl}-2-azaspiro[3.3]heptane-2-carboxylate;
   Ethyl 6-{4-[(2R)-2-(1,3-oxazol-5-yl)pyrrolidin-1-yl]piperidin-1-yl}-2-azaspiro[3.3]heptane-2-carboxylate;
   Ethyl 6-{4-[(2R)-2-(3-methyl-2-oxo-2,3-dihydro-1,3-oxazol-5-yl)pyrrolidin-1-yl]piperidin-1-yl}-2-azaspiro[3.3]heptane-2-carboxylate;
   Ethyl 6-{4-[(2S)-2-methyl-5-oxopyrrolidin-1-yl]piperidin-1-yl}-2-azaspiro[3.3]heptane-2-carboxylate;
   Ethyl 6-{4-[(2R)-2-methyl-5-oxopyrrolidin-1-yl]piperidin-1-yl}-2-azaspiro[3.3]heptane-2-carboxylate;
   Ethyl 6-{4-[(2S)-2-ethyl-5-oxopyrrolidin-1-yl]piperidin-1-yl}-2-azaspiro[3.3]heptane-2-carboxylate;
   Ethyl 6-{4-[(2R)-2-ethyl-5-oxopyrrolidin-1-yl]piperidin-1-yl}-2-azaspiro[3.3]heptane-2-carboxylate; and
   Ethyl 6-{4-[(2R)-4,4-difluoro-2-(hydroxymethyl)pyrrolidin-1-yl]piperidin-1-yl}-2-azaspiro[3.3]heptane-2-carboxylate;
   or a salt thereof.

18. The compound according to claim 1, which is ethyl 6-{4-[(2R)-2-(1,3-oxazol-5-yl)pyrrolidin-1-yl]piperidin-1-yl}-2-azaspiro[3.3]heptane-2-carboxylate, or a salt thereof.

* * * * *